(12) United States Patent
Dugger et al.

(10) Patent No.: US 9,902,691 B2
(45) Date of Patent: Feb. 27, 2018

(54) INTERMEDIATES AND METHODS FOR SYNTHESIZING CALICHEAMICIN DERIVATIVES

(71) Applicant: Pfizer Inc., New York, NY (US)

(72) Inventors: Robert Wayne Dugger, Stonington, CT (US); Leo Joseph Letendre, Oakdale, CT (US); Vimalkumar Babubhai Patel, Garnerville, NY (US); Amarnauth Shastrie Prashad, New City, NY (US); Chunchun Zhang, North Potomac, MD (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/030,563

(22) PCT Filed: Oct. 28, 2014

(86) PCT No.: PCT/IB2014/065657
§ 371 (c)(1),
(2) Date: Apr. 19, 2016

(87) PCT Pub. No.: WO2015/063680
PCT Pub. Date: May 7, 2015

(65) Prior Publication Data
US 2016/0251389 A1    Sep. 1, 2016

Related U.S. Application Data

(60) Provisional application No. 61/899,682, filed on Nov. 4, 2013.

(51) Int. Cl.
| | |
|---|---|
| C07C 323/48 | (2006.01) |
| C07C 319/20 | (2006.01) |
| C07C 319/28 | (2006.01) |
| C07C 319/06 | (2006.01) |
| C07C 323/60 | (2006.01) |
| C07D 207/46 | (2006.01) |
| C07H 1/06 | (2006.01) |
| C07H 15/26 | (2006.01) |
| A61K 47/68 | (2017.01) |

(52) U.S. Cl.
CPC ........ *C07C 323/48* (2013.01); *A61K 47/6809* (2017.08); *C07C 319/06* (2013.01); *C07C 319/20* (2013.01); *C07C 319/28* (2013.01); *C07C 323/60* (2013.01); *C07D 207/46* (2013.01); *C07H 1/06* (2013.01); *C07H 15/26* (2013.01)

(58) Field of Classification Search
CPC .................................................. C07C 323/48
See application file for complete search history.

(56) References Cited

U.S. PATENT DOCUMENTS

| | | | |
|---|---|---|---|
| 4,970,198 | A | 11/1990 | Lee et al. |
| 5,053,394 | A | 10/1991 | Ellestad et al. |
| 5,770,701 | A | 6/1998 | McGahren et al. |
| 8,273,862 | B2 | 9/2012 | Moran et al. |

FOREIGN PATENT DOCUMENTS

WO    2008147765 A1    4/2008

OTHER PUBLICATIONS

Ricart, A. Clin Cancer Res. 2011, 17, 6417-6427.*

* cited by examiner

*Primary Examiner* — Matthew P Coughlin
(74) *Attorney, Agent, or Firm* — David Rubin

(57) ABSTRACT

The present invention relates to intermediates of Formula I

Formula I

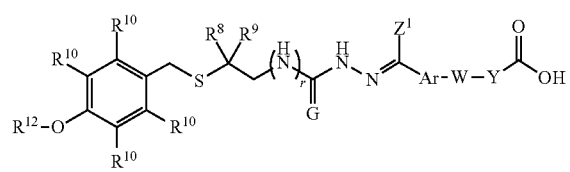

and to methods of synthesizing and purifying calicheamicin derivatives.

5 Claims, No Drawings

INTERMEDIATES AND METHODS FOR SYNTHESIZING CALICHEAMICIN DERIVATIVES

CROSS-REFERENCE TO RELATED APPLICATIONS

This Application is the national stage filing under 35 U.S.C. 371 of Patent Cooperation Treaty Patent Application No. PCT/162014/065657, filed Oct. 28, 2014, which claims the benefit of U.S. Provisional Application No. 61/899,682 filed on Nov. 4, 2013, the contents of each of which are hereby incorporated by reference in their entirety.

FIELD OF THE INVENTION

The invention relates to synthesis of calicheamicin derivatives. The invention also relates to intermediates and linker molecules useful for preparing calicheamicin derivatives and for conjugating a calicheamicin to a biomacromolecule such as a monoclonal antibody.

BACKGROUND OF THE INVENTION

MYLOTARG® (gemtuzumab ozogamicin) consists of a monoclonal antibody against CD33 that is bound to calicheamicin by means of an acid-hydrolyzable linker. The commercial product was marketed as the first antibody-targeted chemotherapeutic agent and was approved for the treatment of acute myeloid leukemia (AML) in elderly patients. Inotuzumab ozogamicin is a CD22 antibody linked to a calicheamicin currently in clinical trials for treatment of certain types of cancer.

The potent family of antibacterial and antitumor agents known collectively as the calicheamicins, or the LL-E33288 complex, are disclosed in U.S. Pat. No. 4,970,198. U.S. Pat. No. 5,053,394 also discloses methyltrisulfide antibacterial and antitumor agents. These compounds in U.S. Pat. No. 4,970,198 and U.S. Pat. No. 5,053,394 contain a methyltrisulfide group that can be reacted with appropriate thiols to form disulfides while at the same time introducing a functional group such as a hydrazide or similar nucleophile. Examples of this reaction with the calicheamicins are given in U.S. Pat. No. 5,053,394. U.S. Pat. No. 5,770,70 is directed to a process for preparing targeted forms of disulfide compounds of the LL-E33288 complex. A linker, 4-(4-acetylphenoxy)butanoic acid, is condensed with an N-acetyl gamma calicheamicin dimethyl hydrazide compound to afford the carboxylic acid-hydrazone which is further treated with N-hydroxysuccinimide to give the OSu ester (N-succinimidyloxy) which is ready for conjugation with a chosen biomacromolecule.

U.S. Pat. No. 8,273,862 describes a synthetic method for constructing linker intermediate molecules (termed "trilinker-activated esters" or "trifunctional linker intermediates" therein). These linker intermediates can be conjugated to calicheamicins to prepare calicheamicin derivatives that can then be further conjugated to biomacromolecules such as monoclonal antibodies. In the steps leading to the preparation of the linker intermediate, the synthetic method described in U.S. Pat. No. 8,273,862 uses a mercapto compound ("compound 2" therein), for example 3-methyl-3-mercaptobutanoic acid hydrazide, as an intermediate.

WO 2008/147765 describes a method for synthesizing the mercapto-containing intermediates, such as 3-methyl-3-mercaptobutanoic acid hydrazide, that are useful in preparing linker intermediates and calicheamicin derivatives as described in the preceding paragraph. WO 2008/147765 alternatively refers to the 3-methyl-3-mercaptobutanoic acid hydrazide as the "DMH linker". WO 2008/147765 notes that 3-methyl-3-mercaptobutanoic acid hydrazide is a preferred mercapto-containing N-acylhydrazine for the purpose of linking calicheamicin to monoclonal antibodies to make, for instance, gemtuzumab ozogamicin or inotuzumab ozogamicin.

In WO 2008/147765, 3-methyl-3-mercaptobutanoic acid hydrazide is prepared by removing the benzyl protecting group from the compound p-methoxybenzylthioether hydrazide under acidic conditions. In order to obtain p-methoxybenzylthioether hydrazide, WO 2008/137765 teaches first reacting p-methoxybenzylthioether acid with oxalyl chloride in methylene chloride to form p-methoxybenzylthioether acid chloride. The p-methoxybenzylthioether acid chloride is then added to a mixture of anhydrous hydrazine and methylene chloride to obtain the p-methoxybenzylthioether hydrazide. However, as is described in WO 2008/147765, the two reactants p-methyloxybenzylthioether acid and p-methoxybenzylthioether acid chloride themselves together generate an undesired by-product, bis-methoxybenzylthioether hydrazide, resulting in lower yield and quality. Furthermore, as described in WO 2008/147765, due to the reactive and unstable nature of the acid chloride molecule p-methoxybenzylthioether acid chloride, anhydrous hydrazine and low temperatures, e.g. −70° C., must be employed.

Another aspect in the preparation of calicheamicin derivatives involves chemically connecting the calicheamicin to the linker molecule. In order to conjugate the calicheamicin to the linker intermediate in U.S. Pat. No. 8,273,862, a final reaction between a calicheamicin and a "trilinker activated ester" (or "trifunctional linker intermediate") is conducted. Structurally, calicheamicins contain a trisulfide moiety, as explained above, that is used in their derivatization, and the chemistry of this reaction between the trisulfide moiety of the calicheamicin and the trilinker activated ester is important in realizing good yields and purity. Previously used sulfur exchange reactions for calicheamicin derivatives have given complex reaction mixtures, multiple byproducts, and low yields.

Finally, the calicheamicin derivative is to be purified after its formation. The process of U.S. Pat. No. 8,273,862 involves purification of the calicheamicin derivative comprising a normal phase chromatography step. The normal phase chromatography step in the purification process described in U.S. Pat. No. 8,273,862 uses methylene chloride as a solvent, and, as stated above, exposure to methylene chloride above various minimum levels is considered to pose potential health hazards. When using normal phase chromatography including methylene chloride, precautions to limit exposure to methylene chloride must therefore be taken.

SUMMARY OF THE INVENTION

The present invention provides new intermediates and methods for synthesizing and purifying linker intermediates that are useful for conjugating calicheamicin antitumor antibiotics to biomacromolecules, such as monoclonal antibodies. The present invention further provides new methods for synthesizing a calicheamicin derivative, which derivative comprises a calicheamicin covalently bonded to a linker. A calicheamicin derivative so prepared can be conjugated to a biomacromolecule, such as a monoclonal antibody to make an antibody-drug conjugate. The intermediates and the synthetic methods of the present invention can for example be used to prepare a calicheamicin derivative for manufacturing gemtuzumab ozogamicin (MYLOTARG®) or inotuzumab ozogamicin.

The subject invention provides improvements to the prior processes for synthesizing and purifying calicheamicin derivatives that overcome some of the problems associated with these prior processes.

As explained above, WO 2008/137765 teaches first reacting an intermediate p-methoxybenzylthioether acid with oxalyl chloride in methylene chloride to form a p-methoxybenzylthioether acid chloride intermediate useful for synthesizing a calicheamicin derivative. In WO 2008/137765, the p-methoxybenzylthioether acid chloride intermediate is then added to a mixture of anhydrous hydrazine and methylene chloride to obtain a p-methoxybenzylthioether hydrazide intermediate. However, as is described in WO 2008/147765, the two reactants p-methyloxybenzylthioether acid and p-methoxybenzylthioether acid chloride themselves together generate an undesired by-product, bis-methoxybenzylthioether hydrazide, resulting in lower yield and quality. The present invention solves this problem of the bis-methoxybenzylthioether hydrazide by-product altogether by avoiding completely the use of p-methoxybenzylthioether acid chloride as an intermediate. By avoiding completely the acid chloride intermediate p-methoxybenzylthioether acid chloride, the subject invention furthermore now permits use of hydrated forms of hydrazine that do not require the same special handling procedures as does anhydrous hydrazine and the new method also avoids the cumbersome requirement of low temperature. Finally, since p-methoxybenzylthioether acid chloride is circumvented in the present invention, methylene chloride and the safety precautions employed therewith need not be used.

The present invention also improves upon the yield of the reaction between the calicheamicin and the linker intermediate compared to the prior processes, such as the process described in U.S. Pat. No. 8,273,862. The present invention improves the yield of the resulting calicheamicin derivative by including a carbodiimide in the reaction.

It has also been discovered, as described herein, that a new method for purifying calicheamicin derivatives can be achieved, which method involves the use of reversed phase high performance liquid chromatography (RP-HPLC), despite the presence of two water-labile groups (hydrazone and N-hydroxysuccinimide ester) on the calicheamicin derivative. This invention thereby overcomes the problems mentioned above associated with purifying calicheamicin derivatives using normal phase chromatography, e.g. using methylene chloride, as described in U.S. Pat. No. 8,273,862.

The present invention, provides compounds of Formula I wherein $R^{12}$ is selected from straight and branched-chain $C_1$-$C_8$ alkyl;

each $R^{10}$ is independently selected from hydrogen, $R^{12}$ and —$OR^{12}$;

$R^8$ and $R^9$ are each independently selected from hydrogen and straight and branched-chain $C_1$-$C_8$ alkyl, wherein each said alkyl for $R^8$ and $R^9$ is independently optionally substituted by —$NH_2$, —$NHR^{11}$, —$NR^{11}R^{13}$, —$OR^{11}$, —OH, or —$SR^{11}$, wherein each $R^{11}$ and each $R^{13}$ are independently selected from straight and branched-chain $C_1$-$C_5$ alkyl;

r is an integer selected from 0 and 1;

G is oxygen or sulfur;

$Z^1$ is H or straight or branched-chain $C_1$-$C_5$ alkyl;

Ar is 1,2-, 1,3-, or 1,4-phenylene optionally substituted with one, two or three groups independently selected from straight or branched-chain $C_1$-$C_6$ alkyl, —$OR^{14}$, —$SR^{14}$, halogen, nitro, —$COOR^{14}$, —$C(=O)NHR^{14}$, —$O(CH_2)_nCOOR^{14}$, —$S(CH_2)_nCOOR^{14}$, —$O(CH_2)_nC(=O)NHR^{14}$, and —$S(CH_2)_nC(=O)NHR^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —$OR^{14}$, —$SR^{14}$, halogen, nitro, —$COOR^{14}$, —$C(=O)NHR^{14}$, —$O(CH_2)_nCOOR^{14}$, —$S(CH_2)_nCOOR^{14}$, —$O(CH_2)_nC(=O)NHR^{14}$, and —$S(CH_2)_nC(=O)NHR^{14}$;

wherein each $R^{14}$ is independently selected from ($C_1$-$C_6$) alkyl and each $R^{14}$ is independently optionally substituted with one or two groups selected from —OH, —($C_1$-$C_4$)alkyl, and —$S(C_1$-$C_4$)alkyl;

each n is an integer independently selected from 0, 1, 2, 3, 4, and 5;

W is selected from —O—, —S—, —C(=O)NH—, —NHC(=O)—, and —$NR^{15}$—, wherein $R^{15}$ is a ($C_1$-$C_5$) alkyl and $R^{15}$ is optionally substituted with one or two groups selected from —OH, —($C_1$-$C_4$)alkyl, and —$S(C_1$-$C_4$)alkyl; and Y is a straight or branched-chain ($C_1$-$C_6$)alkylene group or a straight or branched-chain ($C_2$-$C_6$)alkenylene group.

Compounds of Formula 1 are useful as intermediates for synthesizing linker intermediates and calicheamicin derivatives comprising such linker intermediates, which calicheamicin derivatives can in turn be conjugated to biomacromolecules such as monoclonal antibodies.

In one embodiment of the invention, each $R^{10}$ in the compound of Formula I is hydrogen. In another embodiment, each $R^{10}$ in the compound of Formula I is hydrogen and $R^{12}$ is methyl.

In another embodiment of the invention, the compound of Formula I is a compound having the structure

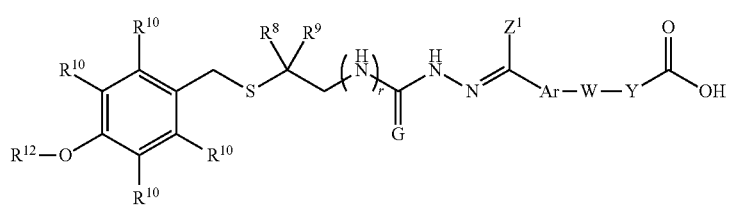

Formula I

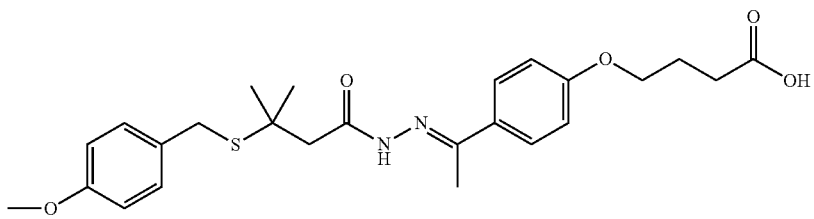 [SMILES: COc1ccc(CSC(C)(C)CC(=O)N/N=C(\C)c2ccc(OCCCC(=O)O)cc2)cc1]

In another embodiment of the invention, $R^8$ and $R^9$ in the compound of Formula I are both methyl, r is 0, G is oxygen, $Z^1$ is methyl, Ar is 1,4-phenylene, W is —O—, and Y is —(CH$_2$)$_3$—.

In another embodiment of the invention $R^8$ and $R^9$ in the compound of Formula I are both methyl.

In another embodiment of the invention, r in the compound of Formula I is 0. In another embodiment of the invention, r in the compound of Formula I is 0 and G is oxygen. In another embodiment of the invention, r in the compound of Formula I is 0 and G is sulfur.

The present invention also provides methods for synthesizing the aforementioned compounds of Formula I, which are as stated useful as intermediates for synthesizing linker intermediates and calicheamicin derivatives comprising said linker intermediate groups. In one embodiment, the present invention provides a method for synthesizing a compound of Formula I Formula I

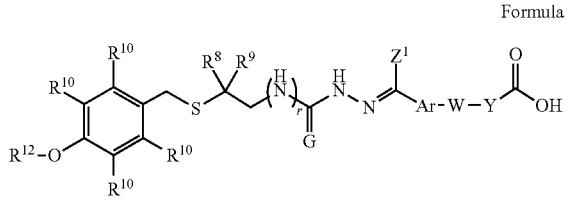

wherein $R^{12}$ is selected from straight and branched-chain $C_1$-$C_8$ alkyl;

each $R^{10}$ is independently selected from hydrogen, $R^{12}$ and —OR$^{12}$;

$R^8$ and $R^9$ are each independently selected from hydrogen and straight and branched-chain $C_1$-$C_8$ alkyl, wherein each said alkyl for $R^8$ and $R^9$ is independently optionally substituted by —NH$_2$, —NHR$^{11}$, —NR$^{11}$R$^{13}$, —OR$^{11}$, —OH, or —SR$^{11}$, wherein each $R^{11}$ and each $R^{13}$ are independently selected from straight and branched-chain $C_1$-$C_5$ alkyl;

r is an integer selected from 0 and 1;

G is oxygen or sulfur;

$Z^1$ is H or straight or branched-chain $C_1$-$C_5$ alkyl;

Ar is 1,2-, 1,3-, or 1,4-phenylene optionally substituted with one, two or three groups independently selected from straight or branched-chain $C_1$-$C_6$ alkyl, —OR$^{14}$, —SR$^{14}$, halogen, nitro, —COOR$^{14}$, —C(=O)NHR$^{14}$, —O(CH$_2$)$_n$COOR$^{14}$, —S(CH$_2$)$_n$COOR$^{14}$, —O(CH$_2$)$_n$C(=O)NHR$^{14}$, and —S(CH$_2$)$_n$C(=O)NHR$^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —OR$^{14}$, —SR$^{14}$, halogen, nitro, —COOR$^{14}$, —C(=O)NHR$^{14}$, —O(CH$_2$)$_n$COOR$^{14}$, —S(CH$_2$)$_n$COOR$^{14}$, —O(CH$_2$)$_n$C(=O)NHR$^{14}$, and —S(CH$_2$)$_n$C(=O)NHR$^{14}$;

wherein each $R^{14}$ is independently selected from ($C_1$-$C_5$) alkyl and each $R^{14}$ is independently optionally substituted with one or two groups selected from —OH, —($C_1$-$C_4$) alkyl, and —S($C_1$-$C_4$)alkyl;

each n is an integer independently selected from 0, 1, 2, 3, 4, and 5;

W is selected from —O—, —S—, —C(=O)NH—, —NHC(=O)—, and —NR$^{15}$—, wherein R$^{15}$ is a ($C_1$-$C_5$) alkyl and R$^{15}$ is optionally substituted with one or two groups selected from —OH, —($C_1$-$C_4$)alkyl, and —S($C_1$-$C_4$)alkyl; and Y is a straight or branched-chain ($C_1$-$C_6$) alkylene group or a straight or branched-chain ($C_2$-$C_6$) alkenylene group; which method comprises reacting a compound of Formula II Formula II

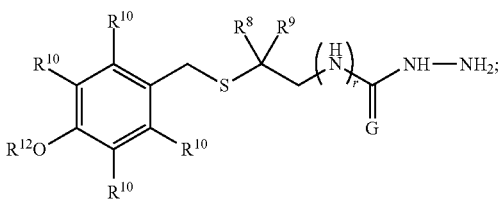

wherein $R^{10}$, $R^{12}$, $R^8$ $R^9$, r and G are as defined above, with a compound of Formula III Formula III

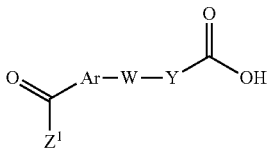

wherein $Z^1$, Ar, W and Y are as defined above. In one embodiment of the method of synthesizing a compound of Formula I, r is 0, G is oxygen, $Z^1$ is methyl, Ar is 1,4-phenylene, W is —O—, and Y is —(CH$_2$)$_3$—. In another embodiment of the method of synthesizing a compound of Formula I, $R^8$ and $R^9$ are methyl. In another embodiment of the method of synthesizing a compound of Formula I, each $R^{10}$ is hydrogen. In another embodiment of the method of synthesizing a compound of Formula I, each $R^{10}$ is hydrogen and $R^{12}$ is methyl.

In another embodiment of the invention for synthesizing a compound of Formula I, $R^8$ and $R^9$ in the compound of Formula II are both methyl.

In another embodiment of the invention for synthesizing a compound of Formula I, r in the compound of Formula II is 0. In another embodiment of the invention for synthesizing a compound of Formula I, r in the compound of Formula II is 0 and G is oxygen. In another embodiment of the invention for synthesizing a compound of Formula I, r in the compound of Formula II is 0 and G is sulfur.

The present invention also provides a method of synthesizing a compound of Formula II Formula II

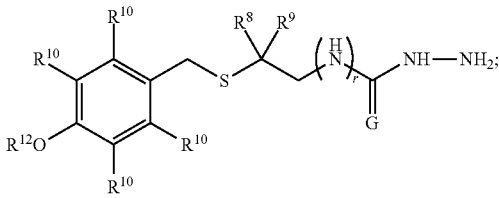

wherein $R^{12}$ is selected from straight and branched-chain $C_1$-$C_8$ alkyl;

each $R^{10}$ is independently selected from hydrogen, $R^{12}$ and —$OR^{12}$;

$R^8$ and $R^9$ are each independently selected from hydrogen and straight and branched-chain $C_1$-$C_8$ alkyl, wherein each said alkyl for $R^8$ and $R^9$ is independently optionally substituted by —$NH_2$, —$NHR^{11}$, —$NR^{11}R^{13}$, —$OR^{11}$, —OH, or —$SR^{11}$, wherein each $R^{11}$ and each $R^{13}$ are independently selected from straight and branched-chain $C_1$-$C_5$ alkyl;

r is an integer selected from 0 and 1; and

G is oxygen or sulfur;

which method comprises treating a compound of Formula VII

Formula VII

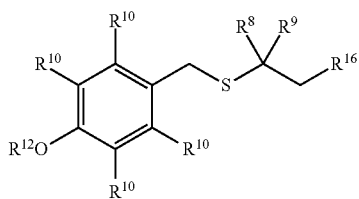

wherein $R^{16}$ is —C(=O)OH or —C(=V)SH, wherein V is oxygen or sulfur, or $R^{16}$ is —$NH_2$;

with an azole activating agent of Formula IX

Formula IX

wherein V' is oxygen or sulfur; and
wherein E is

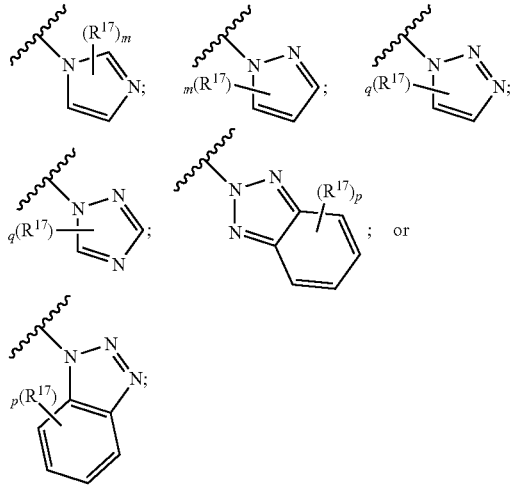

wherein m is an integer 0, 1, 2, or 3; q is an integer 0, 1 or 2; and p is an integer 0, 1, 2, 3, or 4; and wherein each $R^{17}$ attached to E is independently selected from straight and branched-chain ($C_1$-$C_6$)alkyl groups;

in an organic solvent to form a compound of Formula VIII

Formula VIII

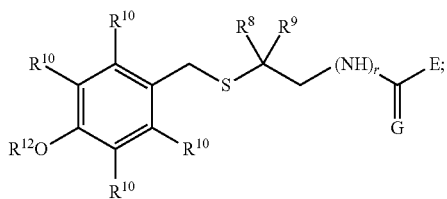

wherein when $R^{16}$ is —C(=O)OH, r is 0 and G is oxygen; when $R^{16}$ is —C(=V)SH, r is 0 and G is V; and when $R^{16}$ is —$NH_2$, r is 1 and G is V';

followed by combining the compound of Formula VIII with hydrazine, thereby forming a compound of Formula II. Compounds of Formula II are useful as intermediates for synthesizing linker intermediates and calicheamicin derivatives comprising said linker intermediate groups, which calicheamicin derivatives can in turn be conjugated to a biomacromolecule, such as a monoclonal antibody.

The azole activating agent is any azole-containing compound of the given Formula IX that will when reacted with a compound of Formula VII afford a compound of Formula VIII wherein E is as described above. Examples of azole activating agents that can be used in the subject invention include carbonyl diimidazole; thiocarbonyl diimidazole; carbonyl bis-pyrazole wherein each pyrazole is optionally substituted with from one to three ($C_1$-$C_6$) alkyl groups; carbonyl bis-1,2,3-triazole; carbonyl bis-benzotriazole, and carbonyl bis-1,2,4-triazole. Preferably, the azole activating agent is carbonyl diimidazole.

The compound of Formula VIII is optionally isolated before combining with hydrazine. In one embodiment, the compound of Formula VIII is not isolated before combining with hydrazine. In another embodiment, the compound of Formula VIII is isolated before combining with hydrazine.

Preferably, $R^{16}$ is —C(=O)OH and the azole activating agent is carbonyl diimidazole.

In one embodiment of the present method for making a compound of Formula II, r is 0 and G is oxygen in the compound of Formula II. In another embodiment of the present method for making a compound of Formula II, r is 0 and G is oxygen in the compound of Formula II and $R^{16}$ in the compound of Formula VII is —C(=O)OH. In a further embodiment of the method for making a compound of Formula II, r is 0 and G is oxygen in the compound of Formula II, $R^{16}$ in Formula VII is —C(=O)OH, and the azole activating agent is carbonyl diimidazole.

In another embodiment of the present method for making a compound of Formula II, the compound of Formula VIII has the structure:

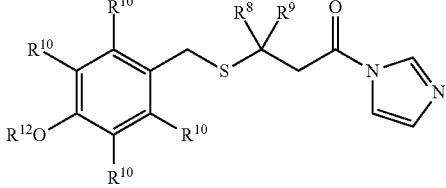

In a further embodiment of the method for making the compound of Formula II, the compound of Formula VIII has the structure:

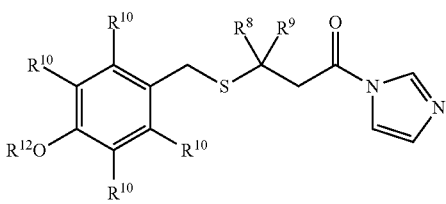

and the azole activating agent is carbonyl diimidazole.

In another embodiment of the invention for synthesizing a compound of Formula II, $R^8$ and $R^9$ in the compound of Formula VII are both methyl.

In another embodiment of the invention for synthesizing a compound of Formula II, the compound of Formula VII comprises $R^{16}$ being —C(=V)SH and V being oxygen or sulfur. It is to be understood that when the compound of Formula VII comprises $R^{16}$ being —C(=V)SH and V being oxygen, such compound of Formula VII can exist in a tautomeric form that is the same compound of Formula VII but wherein $R^{16}$ is —C(=S)OH. When the compound of Formula VII comprises $R^{16}$ being —C(=O)SH, and its tautomer wherein $R^{16}$ is —C(=S)OH, the resulting product compound of Formula II comprises G being oxygen.

In another embodiment of the invention for synthesizing a compound of Formula II, the compound of Formula VII comprises $R^{16}$ being —NH$_2$. When the compound of Formula VII in the method of synthesizing the compound of Formula II comprises $R^{16}$ being —NH$_2$, r in the compound of Formula II resulting from the method is 1. In another embodiment of the method for synthesizing a compound of Formula II, the method comprises a compound of Formula VII wherein $R^{16}$ is —NH$_2$, and a compound of Formula IX, wherein V' is oxygen, the compound of Formula II resulting from said method comprises r being 1 and G being V' (i.e. oxygen). In another embodiment of the method for synthesizing a compound of Formula II, the method comprises a compound of Formula VII wherein $R^{16}$ is —NH$_2$, and a compound of Formula IX, wherein V' is sulfur, the compound of Formula II resulting from said method comprises r being 1 and G being V' (i.e. sulfur).

In another embodiment of the method for synthesizing a compound of Formula II, the method comprises an azole activating agent of Formula IX wherein V' is oxygen. In another embodiment of the method for synthesizing a compound of Formula II, the method comprises an azole activating agent of Formula IX wherein V' is sulfur.

In another embodiment of the method of synthesizing a compound of Formula II, the hydrazine is anhydrous hydrazine. In another embodiment of the method of synthesizing a compound of Formula II, the hydrazine is hydrazine monohydrate. In another embodiment, the hydrazine is an aqueous solution of hydrazine. In another embodiment, the hydrazine is a tetrahydrofuran solution of hydrazine.

As explained above, compounds of Formula I are useful as intermediates for synthesizing linker intermediates and calicheamicin derivatives comprising said linker intermediate groups. Accordingly, the subject invention provides a method for synthesizing compounds of Formula IV, which are also useful as intermediates for synthesizing linker intermediates and calicheamicin derivatives comprising said linker intermediate groups. In one embodiment, the subject invention provides a method for synthesizing a compound of Formula IV Formula IV

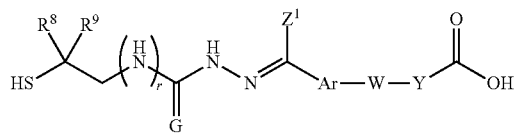

wherein $R^8$ and $R^9$ are each independently selected from hydrogen and straight and branched-chain $C_1$-$C_8$ alkyl, wherein each said alkyl for $R^8$ and $R^9$ is independently optionally substituted by —NH$_2$, —NHR$^{11}$, —NR$^{11}$R$^{13}$, —OR$^{11}$, —OH, or —SR$^{11}$, wherein each R$^{11}$ and each R$^{13}$ are independently selected from straight and branched-chain $C_1$-$C_5$ alkyl;

r is an integer selected from 0 and 1;

G is oxygen or sulfur;

$Z^1$ is H or straight or branched-chain $C_1$-$C_5$ alkyl;

Ar is 1,2-, 1,3-, or 1,4-phenylene optionally substituted with one, two or three groups independently selected from straight or branched-chain $C_1$-$C_6$ alkyl, —OR$^{14}$, —SR$^{14}$, halogen, nitro, —COOR$^{14}$, —C(=O)NHR$^{14}$, —O(CH$_2$)$_n$COOR$^{14}$, —S(CH$_2$)$_n$COOR$^{14}$, —O(CH$_2$)$_n$C(=O)NHR$^{14}$, and —S(CH$_2$)$_n$C(=O)NHR$^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —OR$^{14}$, —SR$^{14}$, halogen, nitro, —COOR$^{14}$, —C(=O)NHR$^{14}$, —O(CH$_2$)$_n$COOR$^{14}$, —S(CH$_2$)$_n$COOR$^{14}$, —O(CH$_2$)$_n$C(=O)NHR$^{14}$, and —S(CH$_2$)$_n$C(=O)NHR$^{14}$;

wherein each $R^{14}$ is independently selected from ($C_1$-$C_5$) alkyl and each $R^{14}$ is independently optionally substituted with one or two groups selected from —OH, —($C_1$-$C_4$)alkyl, and —S($C_1$-$C_4$)alkyl;

each n is an integer independently selected from 0, 1, 2, 3, 4, and 5;

W is selected from —O—, —S—, —C(=O)NH—, —NHC(=O)—, and —NR$^{15}$—, wherein R$^{15}$ is a ($C_1$-$C_5$) alkyl and R$^{15}$ is optionally substituted with one or two groups selected from —OH, —($C_1$-$C_4$)alkyl, and —S($C_1$-$C_4$)alkyl; and Y is a straight or branched-chain ($C_1$-$C_6$) alkylene group or a straight or branched-chain ($C_2$-$C_6$) alkenylene group, which method comprises treating a compound of Formula I Formula I

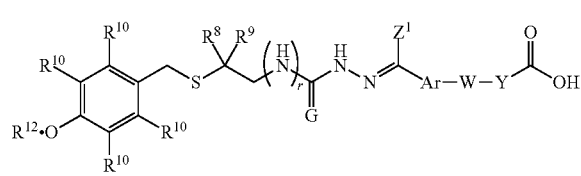

wherein $R^{12}$ is selected from straight and branched-chain $C_1$-$C_8$ alkyl;

each $R^{10}$ is independently selected from hydrogen, $R^{12}$ and —OR$^{12}$;

and $R^8$, $R^9$, r, G, $Z^1$, Ar, W, and Y are as defined;

with a strong acid to form a mixture comprising the compound of Formula IV. The strong acid used in the method for synthesizing a compound of Formula IV can be determined by a person of ordinary skill in the art, as it is any acid that will remove the substituted phenyl-methylene group from the sulfur atom, resulting in the compound of Formula IV. In one embodiment, the strong acid used in the method of the invention for synthesizing the compound of Formula IV is selected from trifluoroacetic acid, sulfuric acid, triflic acid, HCl, HBr, HI. In one embodiment of the method for synthesizing the compound of Formula IV, $R^8$ and $R^9$ are methyl, r is 0, G is oxygen, $Z^1$ is methyl, Ar is 1,4-phenylene, W is —O—, and Y is —(CH$_2$)$_3$—. In another embodiment of the method of synthesizing a compound of Formula IV, each $R^{10}$ is hydrogen. In another embodiment of the method of synthesizing the compound of Formula IV, each $R^{10}$ is hydrogen and $R^{12}$ is methyl.

In another embodiment of the invention for synthesizing a compound of Formula IV, $R^8$ and $R^9$ in the compound of Formula I are both methyl.

In another embodiment of the invention for synthesizing a compound of Formula IV, r in the compound of Formula I is 0. In another embodiment of the invention for synthesizing a compound of Formula IV, r in the compound of Formula I is 0 and G is oxygen. In another embodiment of the invention for synthesizing a compound of Formula IV, r in the compound of Formula I is 0 and G is sulfur.

The invention also provides a method for synthesizing a linker intermediate of Formula V using the intermediates of Formula I and the intermediates of Formula IV. The invention in one embodiment provides a method for synthesizing a linker intermediate of Formula V Formula V

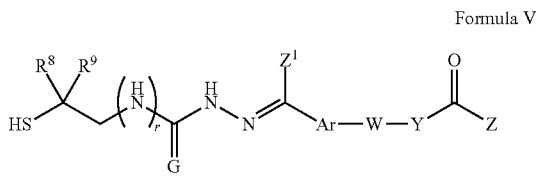

wherein $R^8$ and $R^9$ are each independently selected from hydrogen and straight and branched-chain $C_1$-$C_8$ alkyl, wherein each said alkyl for $R^8$ and $R^9$ is independently optionally substituted by —$NH_2$, —$NHR^{11}$, —$NR^{11}R^{13}$, —$OR^{11}$, —OH, or —$SR^{11}$, wherein each $R^{11}$ and each $R^{13}$ are independently selected from straight and branched-chain $C_1$-$C_5$ alkyl;

r is an integer selected from 0 and 1;

G is oxygen or sulfur;

$Z^1$ is H or straight or branched-chain $C_1$-$C_5$ alkyl;

Ar is 1,2-, 1,3-, or 1,4-phenylene optionally substituted with one, two or three groups independently selected from straight or branched-chain $C_1$-$C_6$ alkyl, —$OR^{14}$, —$SR^{14}$, halogen, nitro, —$COOR^{14}$, —C(=O)$NHR^{14}$, —O$(CH_2)_n COOR^{14}$, —S$(CH_2)_n COOR^{14}$, —O$(CH_2)_n$C(=O)$NHR^{14}$, and —S$(CH_2)_n$C(=O)$NHR^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —$OR^{14}$, —$SR^{14}$, halogen, nitro, —$COOR^{14}$, —C(=O)$NHR^{14}$, —O$(CH_2)_n COOR^{14}$, —S$(CH_2)_n COOR^{14}$, —O$(CH_2)_n$C(=O)$NHR^{14}$, and —S$(CH_2)_n$C(=O)$NHR^{14}$;

wherein each $R^{14}$ is independently selected from ($C_1$-$C_5$) alkyl and each $R^{14}$ is independently optionally substituted with one or two groups selected from —OH, —($C_1$-$C_4$) alkyl, and —S($C_1$-$C_4$)alkyl;

each n is an integer independently selected from 0, 1, 2, 3, 4, and 5;

W is selected from —O—, —S—, —C(=O)NH—, —NHC(=O)—, and —$NR^{15}$—, wherein $R^{15}$ is a ($C_1$-$C_5$) alkyl and $R^{15}$ is optionally substituted with one or two groups selected from —OH, —($C_1$-$C_4$)alkyl, and —S($C_1$-$C_4$)alkyl;

Y is a straight or branched-chain ($C_1$-$C_6$)alkylene group or a straight or branched-chain ($C_2$-$C_6$)alkenylene group; and Z is selected from the group consisting of

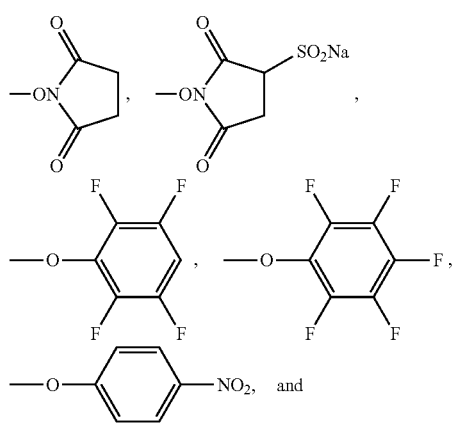

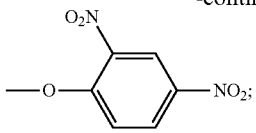

which method comprises a) treating a compound of Formula I

Formula I

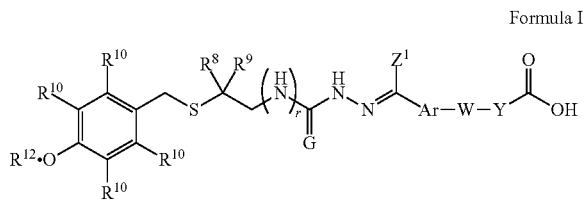

wherein $R^{12}$ is selected from straight and branched-chain $C_1$-$C_8$ alkyl, and each $R^{10}$ is independently selected from hydrogen, $R^{12}$ and —$OR^{12}$;

with a strong acid to form a mixture comprising a compound of Formula IV

Formula VI

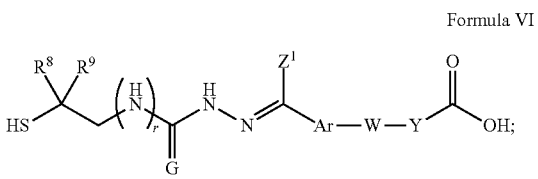

and b) reacting the compound of Formula IV with a compound ZH;

thereby synthesizing the linker intermediate of Formula V. In one embodiment of the method of synthesizing the linker intermediates of Formula V, the strong acid is trifluoroacetic acid or sulfuric acid.

In another embodiment of the invention for synthesizing a linker intermediate of Formula V, $R^8$ and $R^9$ in the compound of Formula I are both methyl.

In another embodiment of the invention for synthesizing a linker intermediate of Formula V, r in the compound of Formula I is 0. In another embodiment of the invention for synthesizing a linker intermediate of Formula V, r in the compound of Formula I is 0 and G is oxygen. In another embodiment of the invention for synthesizing a liner intermediate of Formula V, r in the compound of Formula I is 0 and G is sulfur.

In another embodiment of the method of synthesizing the linker intermediates of Formula V, ZH is

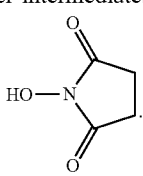

In another embodiment of the method of synthesizing the linker intermediate of Formula V, the linker intermediate is a compound having the structure

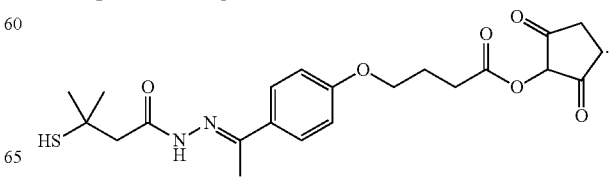

In another embodiment of the method of synthesizing the linker intermediates of Formula V, the compound of Formula I used in the method is obtained by reacting a compound of Formula II Formula II

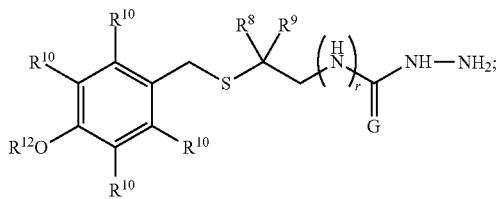

with a compound of Formula III

Formula III

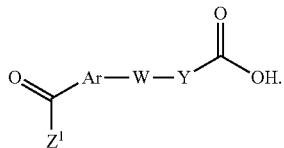

As explained, the linker intermediates are useful for preparing calicheamicin derivatives comprising said linker intermediate groups. The calicheamicin derivatives can in turn be conjugated to biomacromolecules such as monoclonal antibodies. Accordingly, the compounds of Formula I and the methods of synthesis described herein are useful for making such calicheamicin derivatives. The present invention thus provides a method of synthesizing a calicheamicin derivative of Formula VI Formula VI

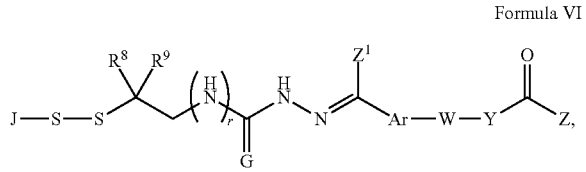

wherein J is

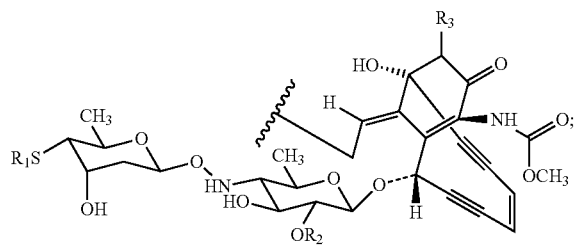

$R_1$ is

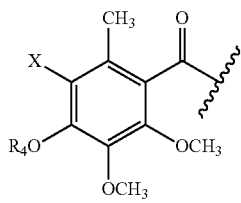

or $CH_3$; $R_2$ is

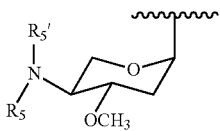

or H;
$R_3$ is

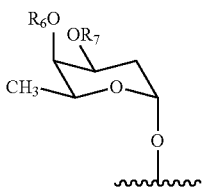

or H; $R_4$ is

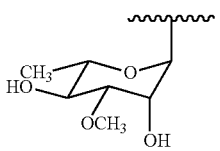 [SMILES: *C1OC(C)C(O)C(OC)C1O]

or H;
$R^5$ is $-CH_3$, $-C_2H_5$, or $-CH(CH_3)_2$;
X is an iodine or bromine atom;
$R^{5'}$ is a hydrogen or the group RCO, wherein R is hydrogen, branched or unbranched alkyl of 1 to 10 carbon atoms, alkylene of 2 to 10 carbon atoms, aryl of 6 to 11 carbon atoms, a ($C_6$-$C_{11}$) aryl-alkyl ($C_1$-$C_5$) group, or a heteroaryl or heteroaryl-alkyl ($C_1$-$C_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, ($C_1$-$C_3$) alkoxy, or thioalkoxy of 1 to 5 carbon atoms;
$R_6$ and $R_7$ are each independently selected from H and

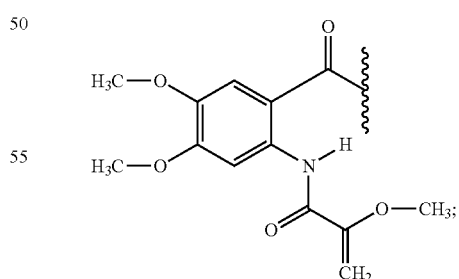

$R^8$ and $R^9$ are each independently selected from hydrogen and straight and branched-chain $C_1$-$C_8$ alkyl, wherein each said alkyl for $R^8$ and $R^9$ is independently optionally substituted by $-NH_2$, $-NHR^{11}$, $-NR^{11}R^{13}$, $-OR^{11}$, $-OH$, or $-SR^{11}$, wherein each $R^{11}$ and each $R^{13}$ are independently selected from straight and branched-chain $C_1$-$C_5$ alkyl;

r is an integer 0 or 1;
G is oxygen or sulfur;
$Z^1$ is H or straight or branched-chain $C_1$-$C_5$ alkyl;
Ar is 1,2-, 1,3-, or 1,4-phenylene optionally substituted with one, two or three groups independently selected from straight or branched-chain $C_1$-$C_6$ alkyl, —$OR^{14}$, —$SR^{14}$, halogen, nitro, —$COOR^{14}$, —$C(=O)NHR^{14}$, —$O(CH_2)_nCOOR^{14}$, —$S(CH_2)_nCOOR^{14}$, —$O(CH_2)_nC(=O)NHR^{14}$, and —$S(CH_2)_nC(=O)NHR^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —$OR^{14}$, —$SR^{14}$, halogen, nitro, —$COOR^{14}$, —$C(=O)NHR^{14}$, —$O(CH_2)_nCOOR^{14}$, —$S(CH_2)_nCOOR^{14}$, —$O(CH_2)_nC(=O)NHR^{14}$, and —$S(CH_2)_nC(=O)NHR^{14}$;

wherein each $R^{14}$ is independently selected from ($C_1$-$C_5$) alkyl and each $R^{14}$ is independently optionally substituted with one or two groups selected from —OH, —($C_1$-$C_4$)alkyl, and —$S(C_1$-$C_4)$alkyl;

each n is an integer independently selected from 0, 1, 2, 3, 4, and 5;

W is selected from —O—, —S—, —C(=O)NH—, —NHC(=O)—, and —$NR^{15}$—, wherein $R^{15}$ is a ($C_1$-$C_5$) alkyl and $R^{15}$ is optionally substituted with one or two groups selected from —OH, —($C_1$-$C_4$)alkyl, and —$S(C_1$-$C_4)$alkyl;

Y is a straight or branched-chain ($C_1$-$C_6$)alkylene group or a straight or branched-chain ($C_2$-$C_6$)alkenylene group; and Z is selected from the group consisting of

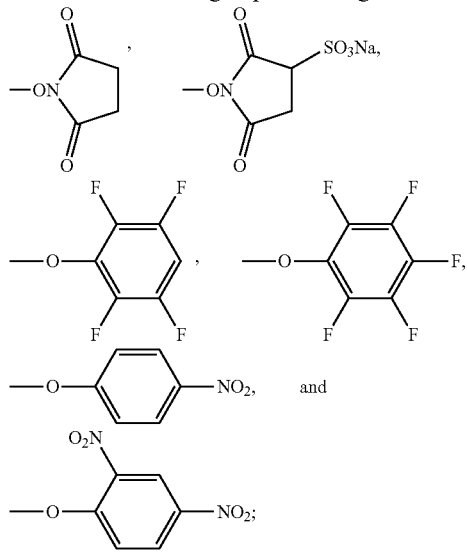

which method comprises
a) treating a compound of Formula I

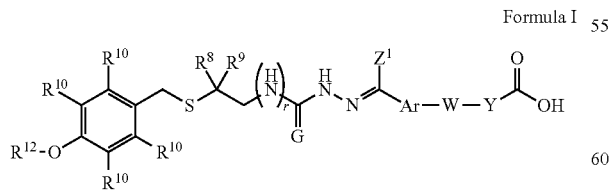

wherein $R^{12}$ is selected from straight and branched-chain $C_1$-$C_8$ alkyl,
and each $R^{10}$ is independently selected from hydrogen, $R^{12}$ and —$OR^{12}$; with a strong acid to form a mixture comprising a compound of Formula IV

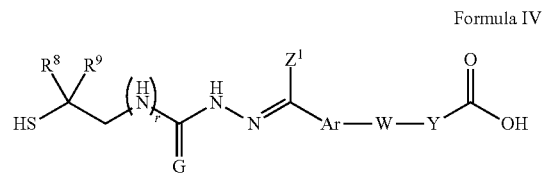

b) reacting the compound of Formula IV with a compound ZH;
to form a linker intermediate of Formula V

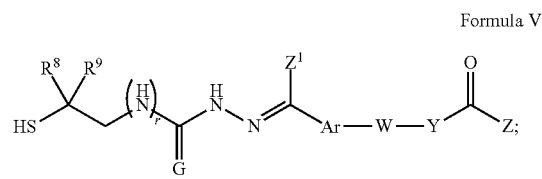

and
c) reacting the linker intermediate of Formula V resulting from step (b) with a methyltrisulfide compound $CH_3$—S—S—S-J;

thereby synthesizing a calicheamicin derivative of Formula VI. In one embodiment of the method of synthesizing the calicheamicin derivative of Formula VI, the strong acid is sulfuric acid or trifluoroacetic acid. In another embodiment of the method of synthesizing the calicheamicin derivative of Formula VI, $R^8$ and $R^9$ are methyl, r is 0, G is oxygen, $Z^1$ is methyl, Ar is 1,4-phenylene, W is —O—, and Y is —$(CH_2)_3$—. In another embodiment of the method of synthesizing a calicheamicin derivative Formula VI, each $R^{10}$ is hydrogen. In another embodiment of the method of synthesizing the calicheamicin derivative of Formula VI, each $R^{10}$ is hydrogen and $R^{12}$ is methyl.

In another embodiment of the invention for synthesizing a calicheamicin derivative of Formula VI, $R^8$ and $R^9$ in the compound of Formula I are both methyl.

In another embodiment of the invention for synthesizing a calicheamicin derivative of Formula VI, r in the compound of Formula I is 0. In another embodiment of the invention for synthesizing a calicheamicin derivative of Formula VI, r in the compound of Formula I is 0 and G is oxygen. In another embodiment of the invention for synthesizing a calicheamicin derivative of Formula VI, r in the compound of Formula I is 0 and G is sulfur.

In another embodiment of the method of synthesizing the calicheamicin derivative of Formula VI, the compound of Formula I is obtained by reacting a compound of Formula II

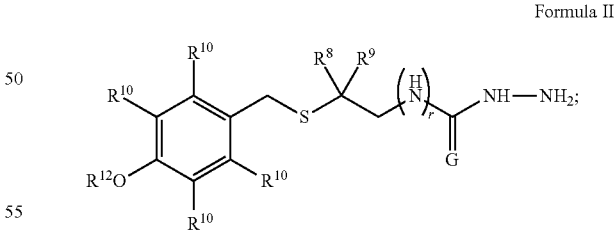

with a compound of Formula III

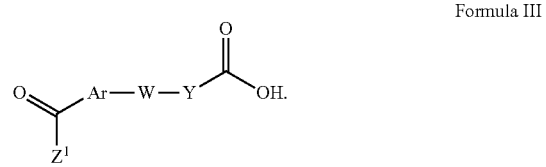

In another embodiment of the method of synthesizing the calicheamicin derivative of Formula VI, one of $R_6$ and $R_7$ is hydrogen and the other of $R_6$ and $R_7$ is

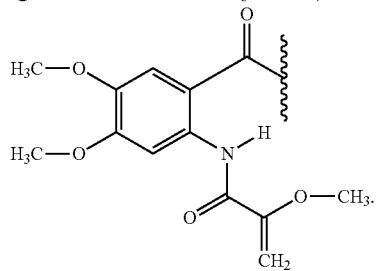

In one embodiment of the intermediates of Formula I and the methods of synthesis of the present invention, $Z^1$ is methyl. In another embodiment of the intermediates and methods of synthesis of the present invention, r is 0 and G is oxygen. In another embodiment of the intermediates and methods of synthesis of the present invention, $Z^1$ is methyl, r is 0 and G is oxygen.

In another embodiment of the methods of synthesis of the present invention, J is an ozogamicin moiety.

In another embodiment of the methods of synthesis of the present invention, the calicheamicin derivative of Formula VI has the structure

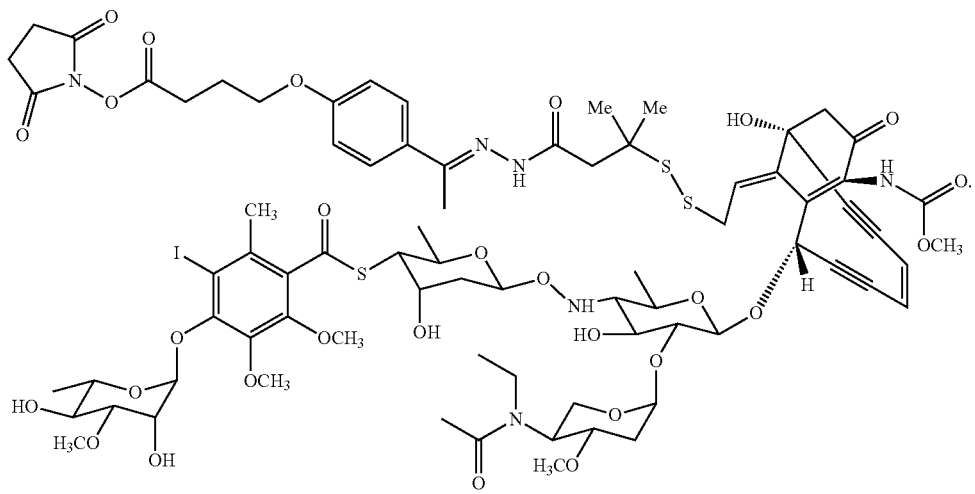

The calicheamicin derivatives of Formula VI synthesized from the methods of the present invention can be conjugated to a biomacromolecule, for example to a monoclonal antibody. The calicheamicin derivatives of Formula VI synthesized from the methods of the present invention can for example be conjugated to the monoclonal anti-CD22 antibody inotuzumab (an antibody specifically binding to the CD22 antigen expressed on the surface of certain cancer cells) or to the anti-CD33 antibody gemtuzumab (an antibody specifically targeting the anti-CD33 antigen expressed on the surface of certain cancer cells). The calicheamicin derivatives of Formula VI synthesized from the methods of the present invention, when conjugated to a monoclonal antibody, in one embodiment have the structure:

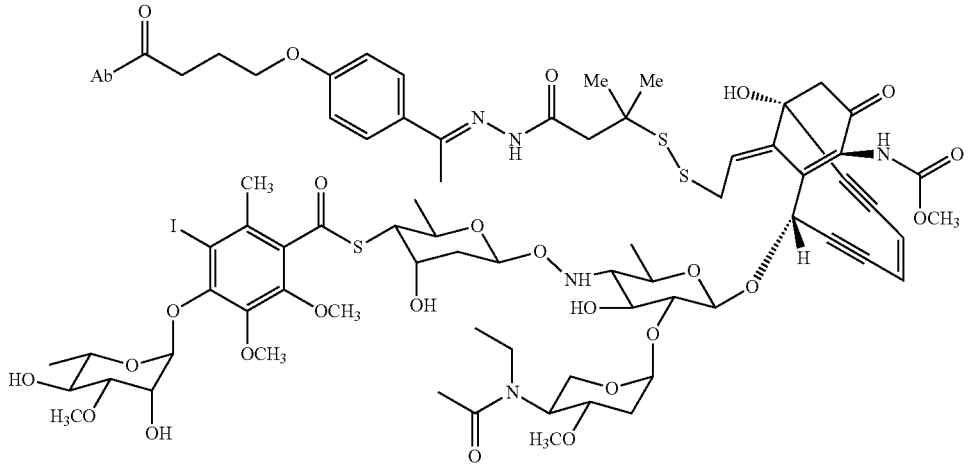

wherein Ab is a monoclonal antibody. Examples of the monoclonal antibody Ab include, but are not limited to, gemtuzumab and inotuzumab.

The terms used in this specification generally have their ordinary meanings in the art, within the context of the invention, and in the specific context where each term is used.

The term "calicheamicin derivative", as used herein, unless otherwise indicated, refers to a derivative of a compound of the formula CH$_3$—S—S—S-J, wherein J is as defined herein, which derivative comprises a calicheamicin moiety —S—S-J bonded to a linker intermediate group:

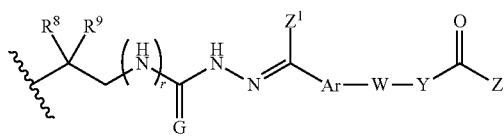

wherein $R^8$, $R^9$, r, G, $Z^1$, Ar, W, Y and Z are as defined herein. The calicheamicin derivative can be further conjugated (i.e. covalently bonded), at the end containing the —C(═O)Z moiety, to a biomacromolecule, such as a monoclonal antibody. Examples of compounds of formula CH3-S—S—S-J are described for example in U.S. Pat. No. 4,970,198 and U.S. Pat. No. 5,053,394, both of which are incorporated herein in their entireties by reference. An example of a compound CH$_3$—S—S—S-J is the calicheamicin ozogamicin.

The term "linker intermediate", as used herein, unless otherwise indicated, refers to those isolated molecules of Formula V described herein, which are capable of being covalently bonded at one end thereof to a molecule of formula CH$_3$—S—S—S-J, and which have a functional group on the other end (the —C(═O)Z end) to which can be covalently bonded a biomacromolecule, such as a monoclonal antibody. The isolated linker intermediates are useful as components for making calichemicin derivatives and calicheamicin linked to a biomacromolecule such as a monoclonal antibody.

Unless otherwise indicated, the term "alkyl" by itself or as part of another term refers to a straight chain or branched, saturated or unsaturated hydrocarbon having the indicated number of carbon atoms (e.g., "$C_1$-$C_8$" alkyl refers to an alkyl group having from 1 to 8 carbon atoms). When the number of carbon atoms is not indicated, the alkyl group has from 1 to 8 carbon atoms (unless it is unsaturated, in which case the alkyl group will have from 2 to 8 carbon atoms). Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

Unless otherwise indicated, "alkylene," by itself or as part of another term, refers to a saturated branched or straight chain or cyclic hydrocarbon radical of the stated number of carbon atoms, having two monovalent radical centers derived by the removal of two hydrogen atoms from the same or two different carbon atoms of a parent alkane. In one embodiment, "alkylene" refers to a saturated branched or straight chain alkylene radical of the stated number of carbon atoms having two monovalent radical centers. Typical alkylene radicals include, but are not limited to: methylene (—CH$_2$—), 1,2-ethylene —CH$_2$CH$_2$—), 1,3-propylene (—CH$_2$CH$_2$CH$_2$—), 1,4-butylene (—CH$_2$CH$_2$CH$_2$CH$_2$—), and the like. The term "alkenylene" refers to a branched or straight chain or cyclic hydrocarbon radical of the stated number of carbon atoms, but having least two carbon atoms connected by a double bond, wherein the radical has two monovalent radical centers derived by the removal of two hydrogen atoms from two different carbon atoms of a parent alkane. In one embodiment, "alkylene" refers to a branched or straight chain radical of the stated number of carbon atoms, but having at least two carbon atoms connected by a double bond, wherein the radical has two monovalent radical centers. Examples of alkenylene radicals include, but are not limited to, —CH═CH—, —CH$_2$CH═CH—, and —CH(CH$_3$)CH═CH.

Unless otherwise indicated, "aryl," by itself or as part of another term, means a carbocyclic aromatic hydrocarbon radical of 6-20, preferably 6-14, carbon atoms derived by the removal of one hydrogen atom from each of one or more carbon atoms of a parent aromatic ring system. Typical aryl groups include, but are not limited to, radicals derived from benzene, naphthalene, anthracene, biphenyl, and the like. If indicated, an aryl group herein can be optionally substituted. The term "arylene" refers to a divalent radical derived from an aryl group as defined herein.

"Halogen" refers to a fluorine, chlorine, bromine or iodine atom.

The present invention also provides a method of synthesizing a calicheamicin derivative of Formula VI Formula VI

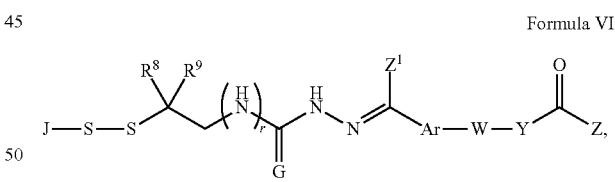

wherein J is

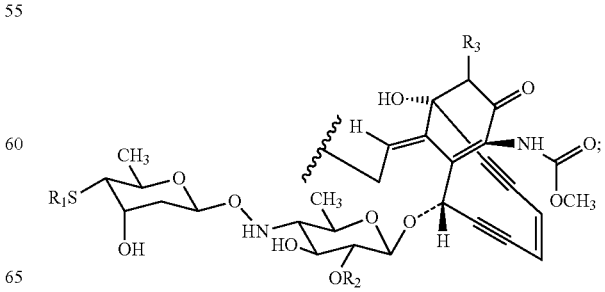

$R_1$ is

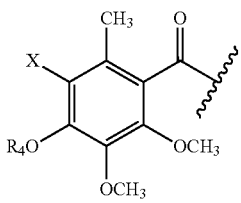

or $CH_3$; $R_2$ is

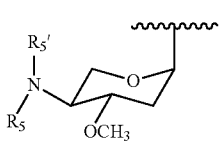

or H;

$R_3$ is

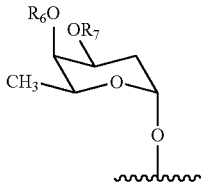

or H; $R_4$ is

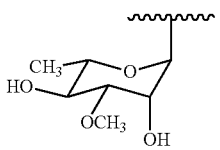

or H;

$R^5$ is —$CH_3$, —$C_2H_5$, or —$CH(CH_3)_2$;

X is an iodine or bromine atom;

$R^{5'}$ is a hydrogen or the group RCO, wherein R is hydrogen, branched or unbranched alkyl of 1 to 10 carbon atoms, alkylene of 2 to 10 carbon atoms, aryl of 6 to 11 carbon atoms, a ($C_6$-$C_{11}$) aryl-alkyl ($C_1$-$C_5$) group, or a heteroaryl or heteroaryl-alkyl ($C_1$-$C_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, ($C_1$-$C_3$) alkoxy, or thioalkoxy of 1 to 5 carbon atoms;

$R_6$ and $R_7$ are each independently selected from H and

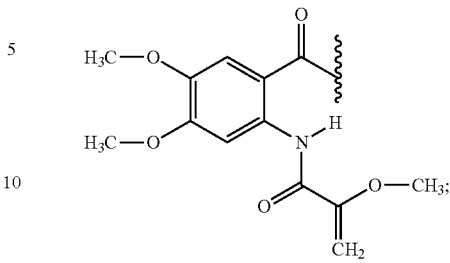

$R^8$ and $R^9$ are each independently selected from hydrogen and straight and branched-chain $C_1$-$C_8$ alkyl, wherein each said alkyl for $R^8$ and $R^9$ is independently optionally substituted by —$NH_2$, —$NHR^{11}$, —$NR^{11}R^{13}$, —$OR^{11}$, —OH, or —$SR^{11}$, wherein each $R^{11}$ and each $R^{13}$ are independently selected from straight and branched-chain $C_1$-$C_5$ alkyl;

r is an integer 0 or 1;

G is oxygen or sulfur;

$Z^1$ is H or straight or branched-chain $C_1$-$C_5$ alkyl;

Ar is 1,2-, 1,3-, or 1,4-phenylene optionally substituted with one, two or three groups independently selected from straight or branched-chain $C_1$-$C_6$ alkyl, —$OR^{14}$, —$SR^{14}$, halogen, nitro, —$COOR^{14}$, —C(=O)$NHR^{14}$, —O($CH_2$)$_n$$COOR^{14}$, —S($CH_2$)$_n$$COOR^{14}$, —O($CH_2$)$_n$C(=O)$NHR^{14}$, and —S($CH_2$)$_n$C(=O)$NHR^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —$OR^{14}$, —$SR^{14}$, halogen, nitro, —$COOR^{14}$, —C(=O)$NHR^{14}$, —O($CH_2$)$_n$$COOR^{14}$, —S($CH_2$)$_n$$COOR^{14}$, —O($CH_2$)$_n$C(=O)$NHR^{14}$, and —S($CH_2$)$_n$C(=O)$NHR^{14}$;

wherein each $R^{14}$ is independently selected from ($C_1$-$C_5$) alkyl and each $R^{14}$ is independently optionally substituted with one or two groups selected from —OH, —($C_1$-$C_4$) alkyl, and —S($C_1$-$C_4$)alkyl;

each n is an integer independently selected from 0, 1, 2, 3, 4, and 5;

W is selected from —O—, —S—, —C(=O)NH—, —NHC(=O)—, and —$NR^{15}$—, wherein $R^{15}$ is a ($C_1$-$C_5$) alkyl and $R^{15}$ is optionally substituted with one or two groups selected from —OH, —($C_1$-$C_4$)alkyl, and —S($C_1$-$C_4$)alkyl;

Y is a straight or branched-chain ($C_1$-$C_6$)alkylene group or a straight or branched-chain ($C_2$-$C_6$)alkenylene group; and Z is selected from the group consisting of

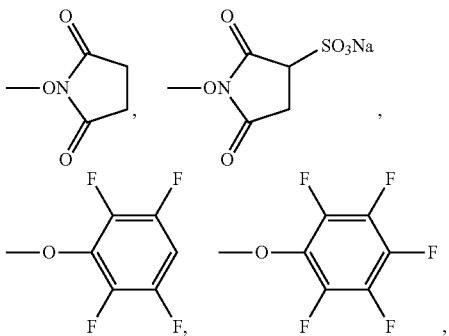

-continued

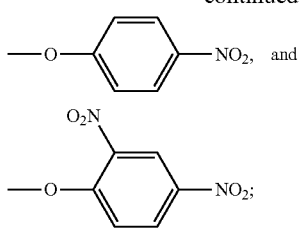

which method comprises reacting a linker intermediate of Formula V

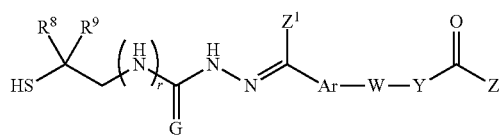

Formula V with a methyltrisulfide compound $CH_3$—S—S—S-J, in the presence of a carbodiimide; thereby synthesizing a calicheamicin derivative of Formula VI.

The present invention also provides a method of synthesizing a calicheamicin derivative of Formula X

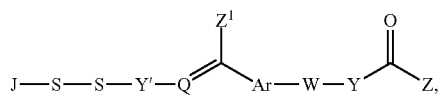

Formula X wherein J is

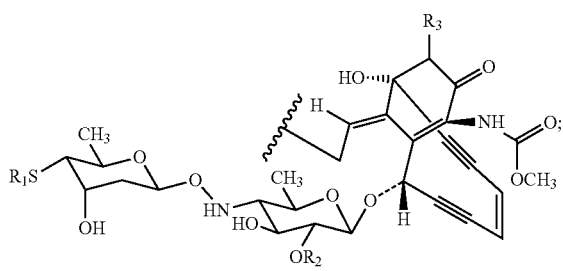

$R_1$ is

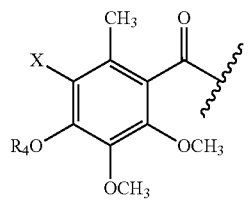

or $CH_3$; $R_2$ is

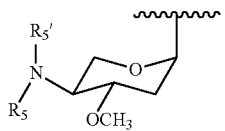

or H;
$R_3$ is

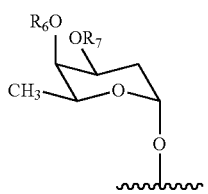

or H; $R_4$ is

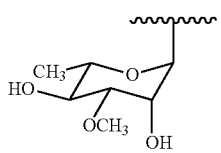

or H;
$R^5$ is —$CH_3$, —$C_2H_5$, or —$CH(CH_3)_2$;
X is an iodine or bromine atom;
$R^{5'}$ is a hydrogen or the group RCO, wherein R is hydrogen, branched or unbranched alkyl of 1 to 10 carbon atoms, alkylene of 2 to 10 carbon atoms, aryl of 6 to 11 carbon atoms, a ($C_6$-$C_{11}$) aryl-alkyl ($C_1$-$C_5$) group, or a heteroaryl or heteroaryl-alkyl ($C_1$-$C_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, ($C_1$-$C_3$) alkoxy, or thioalkoxy of 1 to 5 carbon atoms;
$R_6$ and $R_7$ are each independently selected from H and

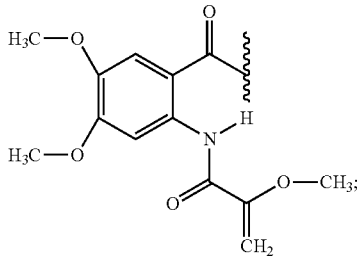 [SMILES: *C(=O)c1cc(OC)c(OC)cc1NC(=O)C(=C)OC]

Y' is a straight or branched-chain ($C_1$-$C_{18}$)alkylene group, a straight or branched-chain ($C_2$-$C_{18}$)alkenylene group, an arylene group, or a heteroarylene group, an arylene ($C_1$-$C_{18}$) alkylene group, an arylene ($C_2$-$C_{18}$)alkenylene group, a heteroarylene ($C_1$-$C_{18}$) alkylene group, or a heteroarylene ($C_1$-$C_{18}$)alkenylene group, wherein said heteroarylene group is a divalent radical derived from furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl, and wherein said Y' can optionally be substituted by dialkylamino of from 1 to 5 carbon atoms, alkoxy of from 1 to 5 carbon atoms, hydroxy, —SH, or alkylthio of from 1 to 5 carbon atoms;

Q is selected from —C(=O)NHN=, —C(=S)NHN=, —NHC(=O)NHN=, —NHC(=S)NHN=, and —O—N=;

$Z^1$ is H or straight or branched-chain $C_1$-$C_5$ alkyl;

Ar is 1,2-, 1,3-, or 1,4-phenylene optionally substituted with one, two or three groups independently selected from straight or branched-chain $C_1$-$C_6$ alkyl, —$OR^{14}$, —$SR^{14}$, halogen, nitro, —$COOR^{14}$, —C(=O)$NHR^{14}$, —O($CH_2$)$_n$$COOR^{14}$, —S($CH_2$)$_n$$COOR^{14}$, —O($CH_2$)$_n$C(=O)$NHR^{14}$, and —S($CH_2$)$_n$C(=O)$NHR^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —$OR^{14}$, —$SR^{14}$, halogen, nitro, —$COOR^{14}$, —C(=O)$NHR^{14}$, —O($CH_2$)$_n$$COOR^{14}$, —S($CH_2$)$_n$$COOR^{14}$, —O($CH_2$)$_n$C(=O)$NHR^{14}$, and —S($CH_2$)$_n$C(=O)$NHR^{14}$;

wherein each $R^{14}$ is independently selected from ($C_1$-$C_5$) alkyl and each $R^{14}$ is independently optionally substituted with one or two groups selected from —OH, —($C_1$-$C_4$) alkyl, and —S($C_1$-$C_4$)alkyl;

each n is an integer independently selected from 0, 1, 2, 3, 4, and 5;

W is selected from —O—, —S—, —C(=O)NH—, —NHC(=O)—, and —$NR^{15}$—, wherein $R^{15}$ is a ($C_1$-$C_5$) alkyl and $R^{15}$ is optionally substituted with one or two groups selected from —OH, —($C_1$-$C_4$)alkyl, and —S($C_1$-$C_4$)alkyl;

Y is a straight or branched-chain ($C_1$-$C_6$)alkylene group or a straight or branched-chain ($C_2$-$C_6$)alkenylene group; and Z is selected from the group consisting of

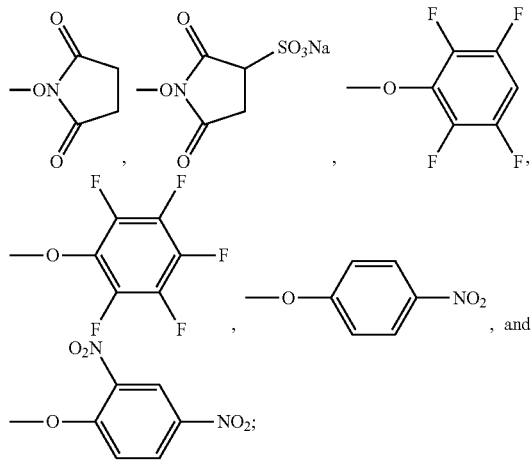

which method comprises reacting a linker intermediate of Formula XI

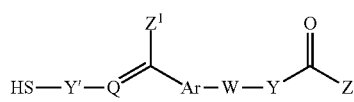

Formula XI with a methyltrisulfide compound $CH_3$—S—S—S-J, in the presence of a carbodiimide; thereby synthesizing a calicheamicin derivative of Formula X.

In one embodiment of this method of synthesizing a calicheamicin derivative of Formula VI or of Formula X in the presence of a carbodiimide, one of $R_6$ and $R_7$ is hydrogen and the other of $R_6$ and $R_7$ is

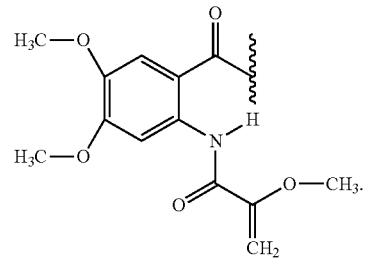 [SMILES: *C(=O)c1cc(OC)c(OC)cc1NC(=O)C(=C)OC]

In another embodiment of the method of the present invention for synthesizing a calicheamicin derivative of Formula VI or of Formula X, the methyltrisulfide has an initial concentration in said reaction with the linker intermediate of Formula V (or of Formula XI as the case may be) of greater than about 3 g/L of the reaction mixture. In another embodiment, the methyltrisulfide compound has an initial concentration in said reaction with the linker intermediate of Formula V (or of Formula XI as the case may be) of between about 10 g/L and 110 g/L of the reaction mixture.

In another embodiment of this method of synthesizing a calicheamicin derivative of Formula VI or of Formula X, the carbodiimide is 1-ethyl-3-(3-dimethylaminopropyl)carbodiimide. The carbodiimide in this method of the invention for synthesizing a calicheamicin derivative of Formula VI or Formula X can be any molecule containing a carbodiimide moiety, and such molecules are known in the art. Examples of carbodiimides that can be used in the present invention include, but are not limited to, 1-ethyl-3-(3-dimethylaminopropyl)carbodiimide (EDC); N,N'-dicyclohexyl carbodiimide (DCC); N,N'-diisopropyl carbodiimide (DIC); N-cylcohexyl-N'-(2-morpholinoethyl) carbodiimide; N-cylcohexyl-N'-[2-(4-methylmorpholin-4-ium-4-yl)ethyl] carbodiimide tosylate; N-cylcohexyl-N'-[4-(diethylmethylammonio)cyclohexyl] carbodiimide tosylate; N,N'-bis(2,2-dimethyl-1,3-dioxolan-4-yl)methyl]carbodiimide; and N-benzyl-N'-isopropylcarbodiimide. Other carbodiimides suitable for employing in the methods of the present invention can be ascertained by those of ordinary skill in the art.

The present invention also provides a method for purifying a calicheamicin derivative of Formula VI or a calicheamicin derivative of Formula X, wherein Formula VI and Formula X are as defined hereinabove, comprising subjecting a calicheamicin derivative of Formula VI or a calicheamicin derivative of Formula X to a reversed phase high performance liquid chromatography (RP-HPLC) purification protocol. It is surprising that a reversed phase purification protocol can be used for purifying the calicheamicin derivative molecules of Formula VI or Formula X considering that these compounds have two water-labile groups, namely a hydrazone group and a N-hydroxy succinimide (NHS) ester group, each group having a different pH dependency for its hydrolysis. Yet, using reversed phase purification is advantageous relative to the normal phase chromatography purification described in the prior art (see U.S. Pat. No. 8,273,862), because the normal phase chromatography uses toxic, environmentally-unfriendly solvent, such as methylene chloride and methanol. The reversed phase high performance liquid chromatography (RP-HPLC) protocol entails use of a C-18 stationary phase that binds the components of the reaction mixture. These components are then eluted and separated using a gradient consisting of aqueous and organic mobile phases ranging in pH from about 4 to about 6 for optimal stability of the two hydrolysable groups present. In one embodiment, the gradient comprises at least two phases. In another embodiment, the gradient comprises 1, 2, 3, 4 or 5 phases. In another embodiment, the gradient comprises 2 or 3 phases. In another embodiment, the gradient comprises 2 phases. Each phase can be organic, aqueous, or a combination thereof. The gradient moves through time from aqueous quality towards increasing organic quality. Aqueous phases known in the art can be used in the subject invention. Examples of aqueous phases that can be used in the subject invention include but are not limited to sodium acetate (NaOAc), sodium succinate, N-methyl morpholine, sodium citrate, and 2-(N-morpholino)ethanesulfonic acid. Organic phases known in the art can be used in the subject invention. Examples of organic phases that can be used in the subject invention include but are not limited to acetonitrile, isopropanol, acetone, dimethoxyethane, and N-methyl-2-pyrrolidone. As stated, any of the phases may comprise a mixture of aqueous and organic quality, for example a mixture of NaOAc and acetonitrile. For example, a mobile phase consisting of 55% 20 mM sodium acetate, pH 5 and 45% acetonitrile is an aqueous/organic mobile phase that can be used for the RP-HPLC purification for the invention. As a further example, an example of a gradient useful in the subject invention is a gradient comprising a first mobile phase consisting of 55% 20 mM sodium acetate, pH 5, and 45% acetonitrile, followed by a second mobile phase consisting of acetonitrile.

In one embodiment of the method of purifying a calicheamicin derivative of Formula VI or of Formula X comprising a RP-HPLC protocol, the calicheamicin derivative of Formula VI or of Formula X comprises Z being selected from:

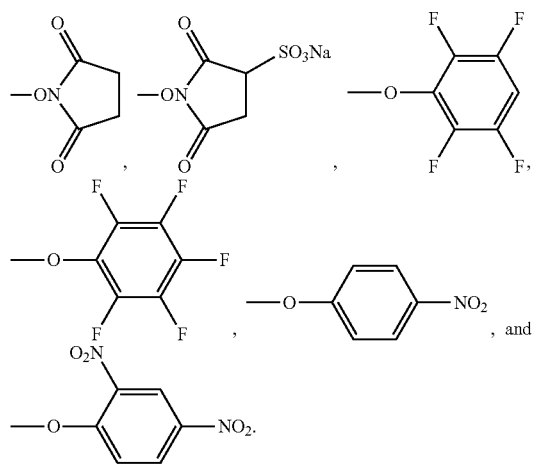

In another embodiment of the method of purifying a calicheamicin derivative of Formula VI or of Formula X comprising a RP-HPLC protocol, the calicheamicin derivative of Formula VI or of Formula X comprises Z being selected from:

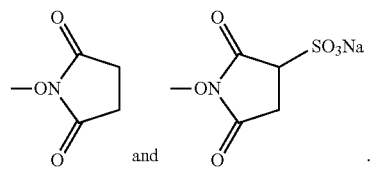

In another embodiment of the method of purifying a calicheamicin derivative of Formula VI or of Formula X comprising a RP-HPLC protocol, the calicheamicin derivative of Formula VI or of Formula X comprises Z being:

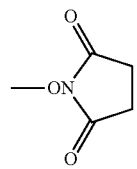

Subsequent to reversed phase purification, the resulting purified calicheamicin derivative can be isolated as described in the art, for example by concentration and partitioning, or the purified calicheamicin derivative can by isolated by using a solid phase extraction (SPE) protocol. A solid phase extraction protocol was identified as an efficient replacement for the dichloromethane partitioning for product isolation from RP-HPLC fractions. In a solid phase extraction, the product is bound to a reversed phase resin by loading in a weak solvent, washed to remove buffer salts (remaining from RP-HPLC purification), and then eluted with organic solvents, such as acetonitrile, affording a concentrated product solution free or substantially free of salts.

Thus, further embodiments of any of the methods of the invention described herein for synthesizing a calicheamicin derivative of Formula VI or of Formula X, comprise furthermore purifying the synthesized calicheamicin derivative of Formula VI or Formula X by subjection to a reversed phase purification protocol. In further embodiments of the invention, a calicheamicin derivative of Formula VI or Formula X resulting from a reversed phase purification protocol is subsequently subjected to a solid phase extraction protocol.

DETAILED DESCRIPTION OF THE INVENTION

The method of the present invention for synthesizing a linker intermediate of Formula V is described in the following reaction Schemes I-IV. In the chemical formulae in Schemes I-IV, $R^8$, $R^9$, $R^{10}$, $R^{12}$, Q, Ar, W, Y, $Z^1$, and Z are as defined above herein.

Scheme I

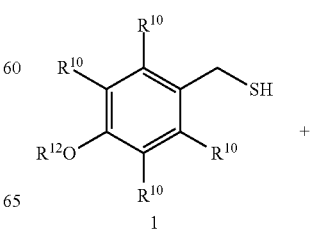

1

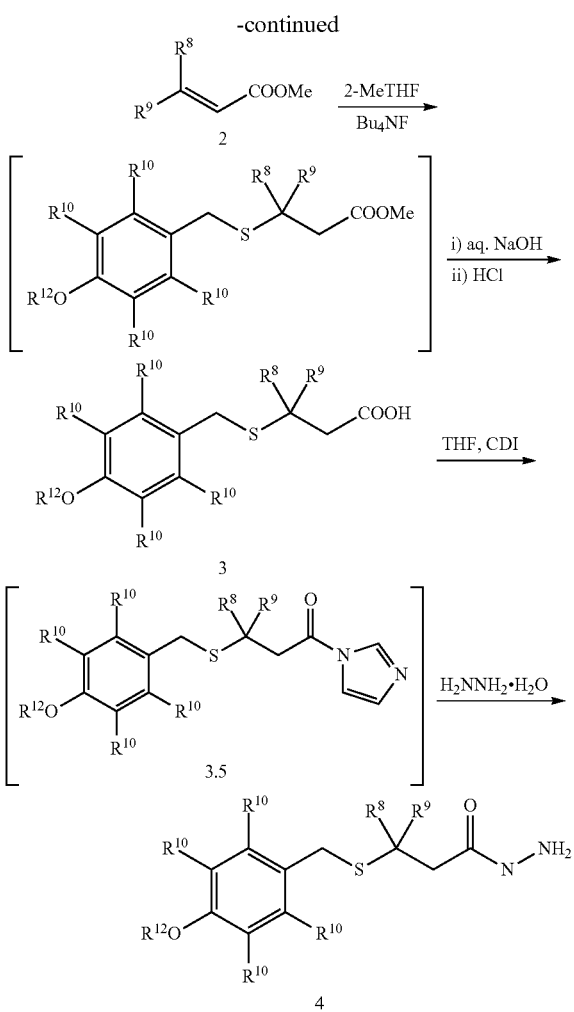

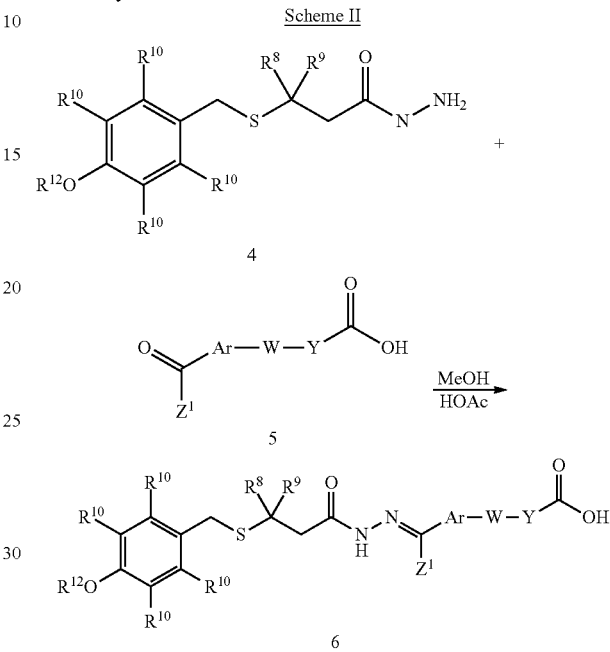

The hydrazine source may be anhydrous hydrazine as is described in WO 2008/147765; however, preferably, the hydrazine source is aqueous hydrazine, such as hydrazine monohydrate. This reaction yields the intermediate compound 4. The compound p-methoxybenzylthioether hydrazide, which is an intermediate compound 4 wherein $R^{12}$ is methyl and each $R^{10}$ is hydrogen, is described in WO 2008/147765, the entire contents of which are incorporated herein by reference.

Referring to Scheme I, a (4-alkoxyphenyl)methanethiol 1, wherein $R^{12}$ is as described herein, is reacted with methyl senecioate 2 to yield the carboxylic acid intermediate compound 3. Intermediate 3 is then charged with a suitable organic solvent such as tetrahydrofuran and an azole activating agent of the Formula IX as described herein, such as carbonyl diimidazole (CDI). Intermediate 3.5 is obtained. This reaction is followed by combining 3.5 with a hydrazine.

In Scheme II, intermediate 4 is reacted with the compound 5 wherein $Z^1$ is as described herein, for example 4-(4-acylphenoxy)butanoic acid, in an inert (in other words, non-reactive) solvent, optionally with an acidic catalyst, to provide the intermediate 6. Examples of inert solvents that may be used in this reaction include, but are not limited to, alcohols (for example, methanol), ethers and esters such as ethyl acetate. A person of ordinary skill in the art can determine a suitable inert solvent for this reaction. Acidic catalysts can also be determined by a person of ordinary skill in the art; examples of acidic catalysts include, but are not limited to acetic acid.

Scheme III

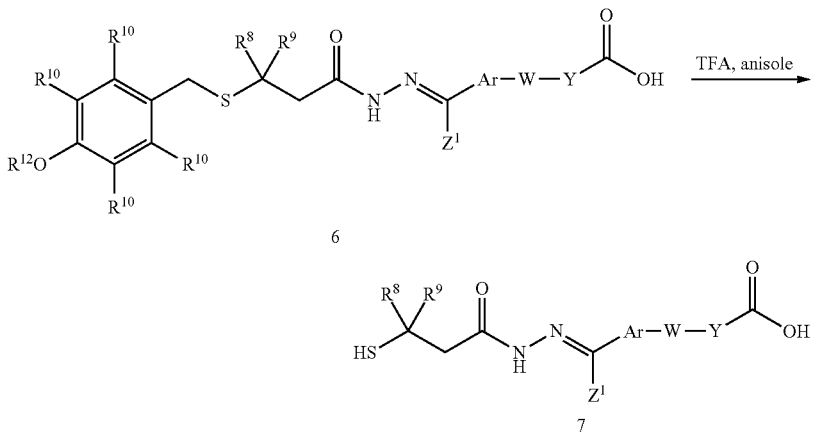

In Scheme III, intermediate compound 6 is deprotected to form compound 7. In this reaction, compound 6 is charged with methoxybenzene and a strong acid optionally under heat, for example trifluoroacetic acid under heat, yielding intermediate compound 7. Other strong acids may be used instead of trifluoroacetic acid, for example sulfuric acid.

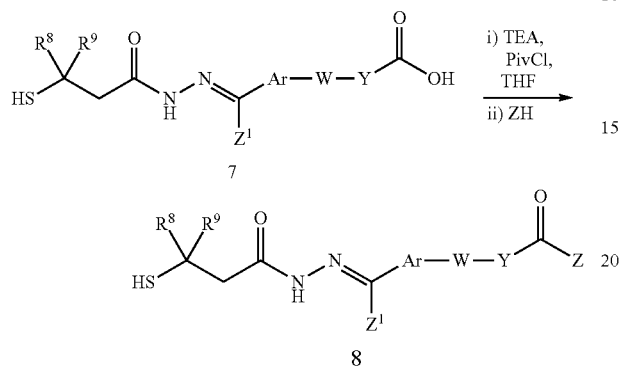

In Scheme IV, intermediate 7 is converted to a compound 8, which is an embodiment of the linker intermediate of Formula V described herein. Intermediate 7 can be converted to a linker intermediate such as 8 as is described in the art, such as in U.S. Pat. No. 8,273,862, which is incorporated herein by reference in its entirety. Preferably, however, as depicted in Scheme IV, intermediate 7 is reacted with a tertiary amine base such as triethylamine (TEA) and with trimethylacetyl chloride (PivCl) in the presence of an inert solvent such as tetrahydrofuran. Subsequently, a compound of Formula ZH, for example N-hydroxysuccinimide, is introduced to provide the linker intermediate 8.

After synthesis of the linker intermediate of Formula V (such as a compound 8), a calicheamicin derivative of Formula VI is then synthesized using the linker intermediate from the reaction of Scheme IV and methods known in the art, for example as is described in U.S. Pat. No. 8,273,862. For example, the linker intermediate of Formula V can be reacted first with an alkali methyl carbonate, which includes but is not limited to sodium carbonate, forming the sodium salt of the linker intermediate in acetonitrile by heating at gentle reflux. Further reaction of the sodium salt of the linker intermediate with the methyltrisulfide $CH_3$—S—S—S-J at about −15° C., in an inert organic solvent, preferably acetonitrile gives the calicheamicin derivative of Formula VI. Preferred is the reaction in acetonitrile at about 0° C. Optionally an organic base may replace the alkali metal carbonate which preferably includes triethylamine, in acetonitrile at about 0° C.

Alternatively, a calicheamicin derivative of Formula VI can be synthesized from the linker intermediate of Formula V by reaction with a molecule of formula $CH_3$—S—S—S-J by using the method described herein comprising a carbodiimide.

The calicheamicin derivative of Formula VI can be further conjugated to a biomacromolecule, such as a monoclonal antibody, to form an antibody-drug conjugate, using techniques described in the art, for example the methods described in U.S. Pat. No. 5,053,394, and in U.S. Pat. No. 5,770,701, both of which are incorporated by reference herein in their entireties.

The following examples are presented to illustrate certain embodiments of the present invention, but should not be construed as limiting the scope of this invention. Those skilled in the art will readily understand that known variations of the specific conditions of the following examples can be used.

EXAMPLE 1

3-(4-methoxybenzylthio)-3-methylbutanoic acid

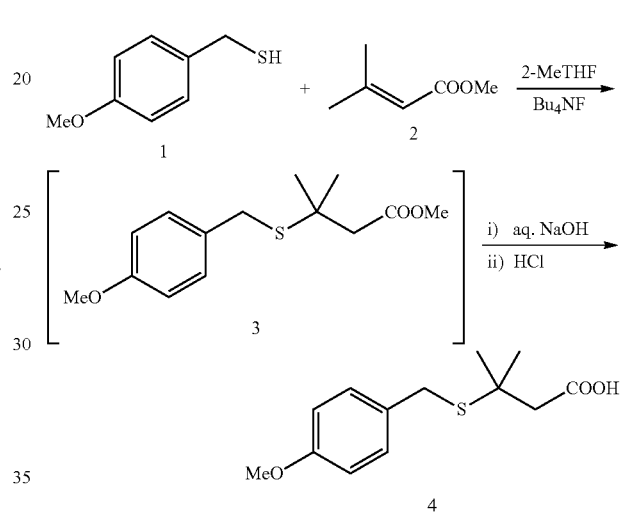

85 g of 1 and 255 mL of 2-Methyltetrahydrofuran were added to a reactor at 20-25° C. 125.05 g of 2 was added to the reactor and the reactor was degassed by bubbling a nitrogen stream into the stirred solution for 15-20 min. Tetrabutylammonium fluoride (1M in THF, 0.05 equiv., 36.1 mL) was added to the reactor and the reaction was maintained at 20-30° C. for 2 hours.

A solution of calcium chloride dihydrate (0.35 equiv., 28.060 g) in 255 mL of water was added. After stirring for 20 minutes the lower aqueous phase was removed. To the upper organic phase was added 252 mL of methanol and 3 equiv. of NaOH in 252 mL of water. The reaction mixture was stirred until complete consumption of the intermediate ester (3) is observed.

The reaction was cooled to 15° C. and 2-methyltetrahydrofuran was added (252 mL) followed by 252 mL of water. Concentrated HCl was added (3.1 equiv., 184 mL) slowly, maintaining the reaction in the range 15-30° C. The lower aqueous phase was removed. The organic layer was washed with 1M HCl (252 mL) and heptanes was added (1940 mL). The solution was distilled to remove 2-methyltetrahydrofuran. The resulting slurry was stirred for an hour, then filtered and dried. The mother liquor was concentrated to give a second crop of solids.

Total yield of the title compound acid 4 was 162.59 g (88.5%). $^1$H NMR (CDCl$_3$): δ (ppm) 1.5 (s, 6H), 2.3 (s, 2H), 3.6 (m, 5H), 6.7 (d, 2H), 7.6 (d, 2H).

EXAMPLE 2

3-(4-methoxybenzylthio)-3-methylbutanehydrazide

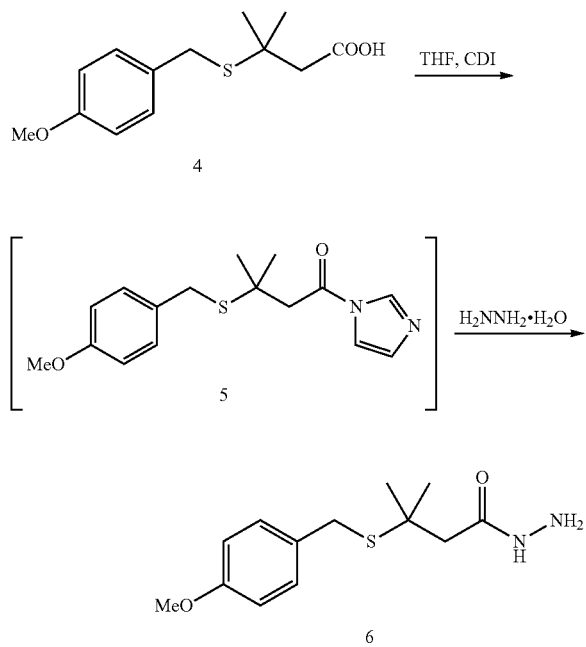

Acid 4 (81.67 g, 321 mmol) was added to 375 mL of THF (tetrahydrofuran). CDI (1.05 eq., 54.7 g) was charged in three portions and the reaction was stirred at 20° C. for 2.5 hours. In a separate reactor a solution of hydrazine monohydrate (2.5 equiv., 40.19 g) in 200 mL of THF was prepared. The solution of intermediate 5 was added to the hydrazine hydrate solution keeping the internal temperature at 20° C. After the addition was complete the reaction was stirred for 18 hours, then concentrated to 100 mL. 850 mL of EtOAc (ethyl acetate) was added, and the solution was washed 3 times with 500 mL of water then 200 mL of brine. The organic layer was dried with $Na_2SO_4$, filtered through diatomaceous earth and concentrated on a rotary evaporator to a white slurry. 300 mL of heptane was added and 200 mL was removed on a rotary evaporator. Another 200 mL of heptane was added and stripped to a thick white slurry. The mixture was filtered, washed with heptanes and dried. 83.15 g (96.5%) of the title compound 6 was obtained from 4. MS 269 (M+1), 121, 120.

EXAMPLE 3

4-(4-(1-(2-(3-(4-methoxybenzylthio)-3-methylbutanoyl)hydrazono)-ethyl)phenoxy)butanoic acid

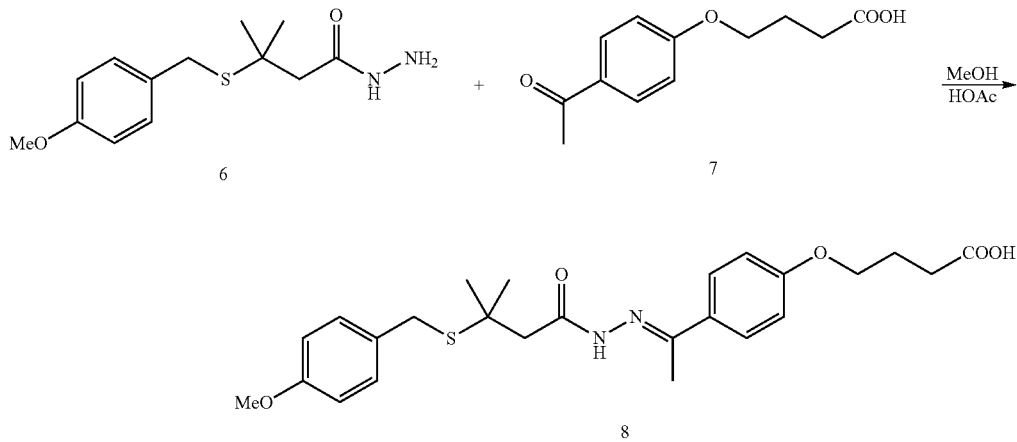 [SMILES: "MeOH" ; COc1ccc(CSC(C)(C)CC(=O)NN)cc1 ; CC(=O)c1ccc(OCCCC(=O)O)cc1 ; COc1ccc(CSC(C)(C)CC(=O)N/N=C(\C)c2ccc(OCCCC(=O)O)cc2)cc1 ; "HOAc"]

68 g of 6 and 57.43 g of 7 were added to 680 mL of methanol (MeOH). 68 mL of acetic acid (HOAc) was added and the mixture was heated at 45° C. for 3 hours, cooled to 20° C., and held for 16 hours. The slurry was filtered, washed with methanol and dried. 112.60 g of the title compound 8 as a mixture of E and Z isomers was obtained. $^1$H NMR (DMSO-$d_6$): δ (ppm) 1.5 (m, 6H), 2.0 (m, 2H), 2.2 (m, 3H), 2.4 (m, 2H), 2.7 (s, 1.1H), 3.0 (s, 0.9H), 3.7 (m, 3H), 3.8 (m, 2H), 4.0 (m, 2H), 6.8 (m 2H), 6.9 (m, 2H), 7.3 (m, 2H), 7.7 (m, 2H), 10.2&10.3 (s, 1H), 12.1 (s, 1H). LC-MS m/z 473 [M+H]$^+$.

EXAMPLE 4

4-(4-(1-(2-(3-mercapto-3-methylbutanoyl)hydrazono)ethyl)-phenoxy)butanoic acid

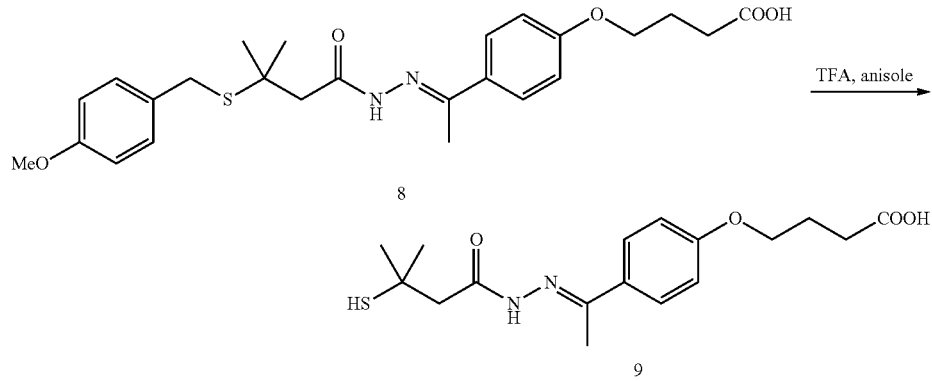

290.5 g, (614.7 mmol) of 8 and 1162 mL of anisole were charged to a reactor at 20-25° C. Trifluoroacetic acid (1162 mL) was added over 2 minutes, and the reaction was heated to 65-70° C. for 2.5 hours. The reaction was cooled to 40° C. The TFA (trifluoroacetic acid) was vacuum distilled and replaced with 2-methyltetrahydrofuran (2905 mL). The distillation was continued until a thick slurry was observed (final volume of the slurry was approximately 2 L). The slurry was cooled to 15° C. and filtered. The crude product was reslurried in methanol (1836.6 mL), heated to 55° C. and then cooled to 20° C. overnight. The slurry was filtered, washed with methanol and dried. 171.80 g (93.54%) of the title compound 9 as an E and Z mixture of isomers was obtained from 8. $^1$H NMR (DMSO-$d_6$): δ (ppm) 1.5 (m, 6H), 2.0 (m, 2H), 2.2 (m, 3H), 2.4 (m, 2H), 2.7 (s, 1.1H), 3.0 (s, 0.9H), 3.3 (s 1H), 4.0 (m, 2H), 6.9 (m, 2H), 7.7 (m, 2H), 10.2&10.3 (s, 1H), 12.1 (s, 1H).

EXAMPLE 5

2,5-dioxopyrrolidin-1-yl-4-(4-(1-(2-(3-mercapto-3-methylbutanoyl)-hydrazono)ethyl)phenoxy)butanoate Reactor setup: 2-L jacketed reactor, Tr probe, nitrogen inlet.

60 g (170.3 mmol) was added to 2400 mL of THF and cooled to 10° C. Triethylamine (2 equiv., 34.46 g) was added, then trimethylacetyl chloride (1.1 equiv., 22.81 g) was added slowly over 10 minutes, maintaining the temperature in the range 10-20° C. The mixture was stirred at 10-20° C. for 30 minutes. N-hydroxysuccinimide (1.1 equiv., 21.99 g) was added to the reactor and stirred at 20-25° C. for 30 minutes.

The slurry was filtered to remove the TEA-HCl salts and concentrated under vacuum to a volume of approximately 800 mL. Hexane (780 mL) was slowly added to crystallize the product. The slurry was stirred for 1.5 hours, then filtered, washed with heptanes and dried. 70.4 g (92% yield) of the title compound linker intermediate 10 was obtained from 9.

The crude product was recrystallized by adding 144 g of 10 to 2100 mL of THF and heated to 60° C. The mixture was filtered through diatomaceous eart, and 2100 mL of hexane slowly added and cooled to 20° C. over 1.5 hours. The slurry was filtered, washed with cold THF/hexane (1:1), then hexane and dried. 126 g (87.5% recovery) of the title

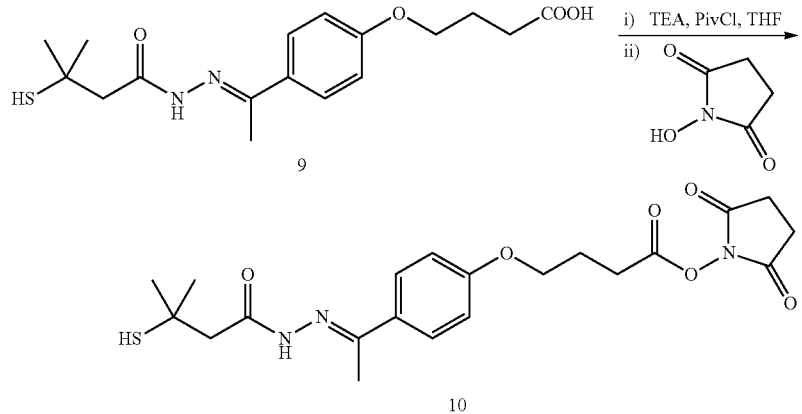

compound linker intermediate 10 was obtained from 9. $^1$H NMR (DMSO-d$_6$): δ (ppm) 1.5 (m, 6H), 2.1 (m, 2H), 2.2 (m, 3H), 2.7 (s, 1.1H), 2.9 (M, 5H) 3.0 (s, 1.9H), 3.3 (s 1H), 4.3 (m, 2H), 7.0 (m, 2H), 7.5 (m, 2H), 10.2&10.3 (s, 1H).

EXAMPLE 6

Preparation of Butanoic acid, 3-[[(2E)-2-[(1R,4Z,8S)-8-[[2-O-[4-(acetylethylamino)-2,4-dideoxy-3-O-methyl-a-L-threo-pentopyranosyl]-4,6-dideoxy-4-[[[2,6-dideoxy-4-S-[4-[(6-deoxy-3-O-methyl-a-L-mannopyranosyl)oxy]-3-iodo-5,6-dimethoxy-2-methylbenzoyl]-4-thio-β-D-ribo-hexopyranosyl]oxy]amino]-β-D-glucopyranosyl]oxy]-1-hydroxy-10-[(methoxycarbonyl)amino]-11-oxobicyclo[7.3.1]trideca-4,9-diene-2,6-diyn-13-ylidene]ethyl]dithio]-3-methyl-, 2-[(1E)-1-[4-[4-[(2,5-dioxo-1-pyrrolidinyl)oxy]-4-oxobutoxy]phenyl]ethylidene] hydrazide To a solution of N-acetyl-calicheamicin (50 mg, 0.035 mmol) in acetonitrile (1.0 mL) at room temperature was added linker intermediate butanoic acid, 3-mercapto-3-methyl-,2-[(E)-1-[4-[4-[(2,5-dioxo-1-pyrrolidinyl)-oxy]-4-oxobutoxy]phenyl]ethylidene]hydrazide (31.9 mg, 0.07 mmol) in one portion followed by 1,(3-dimethylaminopropyl)-3-ethylcarbodiimide (6.7 mg, 0.035 mmol) and then triethylamine (5.3 mg, 7.3 μL, 0.053 mmol). The reaction mixture (a slurry) was stirred for 1 hour at room temperature at which point it became a yellow solution. The yield was determined by area percent relative to a derivative standard (60% yield).

Mass Spec:

(M+Na)=1801.4578

$^1$H NMR:

$^1$H NMR (CDCl$_3$+5% CD$_3$OD, 400 MHz): 8.69 (s, 1H, 18C—NH—N=), 7.75 (d, J=8.7 Hz, 2H, 22), 6.95 (d, J=8.7 Hz, 2H, 23), 6.38 (br t, J=7 Hz, 1H, 14), 6.23 (d, J=1.5 Hz, 1H, 8), 5.90 (d, J=9.5 Hz, 1H, 4), 5.80 (dd, J=9.5, 1.5 Hz, 1H, 5), 5.72 (d, J=1.5 Hz, 1H, 1D), 5.63 (br d, J=2.2 Hz, 1H, 1E), 5.03 (dd, J=11.5, 1.6 Hz, 1H, 1B), 4.70 (m, 1H, 5E), 4.61 (d, J=7.8 Hz, 1H, 1A), 4.6 (m, 1H, 3E), 4.49 (m, 1H, 2D), 4.31 (m, 1H, 3B), 4.20 (m, 1H, 5D), 4.10 (m, 2H, 25), 4.07 (m, 1H, 5B), 4.03 (m, 1H, 3A), 3.91 (m, 1H, 15), 3.89 (s, 3H, 2C—OCH$_3$), 3.84 (s, 3H, 3C—OCH$_3$), 3.8 (m, 1H, 3D), 3.76 (m, 1H, 15), 3.75 (m, 1H, 4B), 3.65 (m, 1H, 5A), 3.63 (bs, 3H, 10-NHCOOCH$_3$), 3.62 (m, 1H, 2A), 3.6 (m, 1H, 4D), 3.57 (s, 3H, 3D-OCH$_3$), 3.4 (m, 1H, 5E), 3.37 (s, 3H, 3E-OCH$_3$), 3.30 (m, 2H, 4E-N—CH$_2$CH$_3$), 3.12 (d, J=17.6 Hz, 1H, 12), 3.0 (m, 1H, 4E), 2.85 (m, 2H, 27), 2.85 (bs, 4, 30), 2.72 (d, J=17.6 Hz, 1H, 12), 2.5 (m, 2H, 17), 2.4 (m, 1H, 2E equatorial), 2.33 (m, 1H, 4A), 2.25 (m, 2H, 26), 2.18 (s, 3H, 19), 2.08 (s, 3H, 4E-N—COCH$_3$), 2.0 (m, 1H, 2B), 1.8 (m, 1H, 2B), 1.50 (s, 3H, 16a), 1.44 (s, 3H, 16b), 1.42 (d, J=6.2 Hz, 3H, 6B), 1.4 (m, 1H, 2E axial), 1.31 (d, J=6.1 Hz, 3H, 6A), 1.31 (d, J=6.1 Hz, 3H, 6D), 1.19 (t, J=7.2 Hz, 3H, 4E-N—CH$_2$CH$_3$).

EXAMPLE 7

Preparation of Butanoic acid, 3-[[(2E)-2-[(1R,4Z,8S)-8-[[2-O-[4-(acetylethylamino)-2,4-dideoxy-3-O-methyl-a-L-threo-pentopyranosyl]-4,6-dideoxy-4-[[[2,6-dideoxy-4-S-[4-[(6-deoxy-3-O-methyl-a-L-mannopyranosyl)oxy]-3-iodo-5,6-dimethoxy-2-methylbenzoyl]-4-thio-β-D-ribo-hexopyranosyl]oxy]amino]-β-D-glucopyranosyl]oxy]-1-hydroxy-10-[(methoxycarbonyl)amino]-11-oxobicyclo[7.3.1]trideca-4,9-diene-2,6-diyn-13-ylidene]ethyl]dithio]-3-methyl-, 2-[(1E)-1-[4-[4-[(2,5-dioxo-1-pyrrolidinyl)oxy]-4-oxobutoxy]phenyl]ethylidene] hydrazide, Without Using EDC As a comparison to the method of the present invention illustrated in Example 6, the following reaction was conducted: To a solution of N-acetyl-calicheamicin (50 mg, 0.035 mmol) in acetonitrile (1.0 mL) at room temperature was added linker intermediate butanoic acid, 3-mercapto-3-methyl-,2-[(E)-1-[4-[4-[(2, 5-dioxo-1-pyrrolidinyl)oxy]-4-oxobutoxy]phenyl]-ethylidene]-hydrazide (31.9 mg, 0.07 mmol) in one portion followed by triethylamine (5.3 mg, 7.3 uL, 0.053 mmol). The reaction mixture (a slurry) was stirred for 1 hour at room temperature at which point it became a yellow solution. The yield was determined by area percent relative to a derivative standard (35% yield).

Mass Spec:

(M+Na)=1801.4578

$^1$H NMR:

$^1$H NMR (CDCl$_3$+5% CD$_3$OD, 400 MHz): 8.69 (s, 1H, 18C—NH—N=), 7.75 (d, J=8.7 Hz, 2H, 22), 6.95 (d, J=8.7 Hz, 2H, 23), 6.38 (br t, J=7 Hz, 1H, 14), 6.23 (d, J=1.5 Hz, 1H, 8), 5.90 (d, J=9.5 Hz, 1H, 4), 5.80 (dd, J=9.5, 1.5 Hz, 1H, 5), 5.72 (d, J=1.5 Hz, 1H, 1D), 5.63 (br d, J=2.2 Hz, 1H, 1E), 5.03 (dd, J=11.5, 1.6 Hz, 1H, 1B), 4.70 (m, 1H, 5E), 4.61 (d, J=7.8 Hz, 1H, 1A), 4.6 (m, 1H, 3E), 4.49 (m, 1H, 2D), 4.31 (m, 1H, 3B), 4.20 (m, 1H, 5D), 4.10 (m, 2H, 25), 4.07 (m, 1H, 5B), 4.03 (m, 1H, 3A), 3.91 (m, 1H, 15), 3.89 (s, 3H, 2C—OCH$_3$), 3.84 (s, 3H, 3C—OCH$_3$), 3.8 (m, 1H, 3D), 3.76 (m, 1H, 15), 3.75 (m, 1H, 4B), 3.65 (m, 1H, 5A), 3.63 (bs, 3H, 10-NHCOOCH$_3$), 3.62 (m, 1H, 2A), 3.6 (m, 1H, 4D), 3.57 (s, 3H, 3D-OCH$_3$), 3.4 (m, 1H, 5E), 3.37 (s, 3H, 3E-OCH$_3$), 3.30 (m, 2H, 4E-N—CH$_2$CH$_3$), 3.12 (d, J=17.6 Hz, 1H, 12), 3.0 (m, 1H, 4E), 2.85 (m, 2H, 27), 2.85 (bs, 4, 30), 2.72 (d, J=17.6 Hz, 1H, 12), 2.5 (m, 2H, 17), 2.4 (m, 1H, 2E equatorial), 2.33 (m, 1H, 4A), 2.25 (m, 2H, 26), 2.18 (s, 3H, 19), 2.08 (s, 3H, 4E-N—COCH$_3$), 2.0 (m, 1H, 2B), 1.8 (m, 1H, 2B), 1.50 (s, 3H, 16a), 1.44 (s, 3H, 16b), 1.42 (d, J=6.2 Hz, 3H, 6B), 1.4 (m, 1H, 2E axial), 1.31 (d, J=6.1 Hz, 3H, 6A), 1.31 (d, J=6.1 Hz, 3H, 6D), 1.19 (t, J=7.2 Hz, 3H, 4E-N—CH$_2$CH$_3$)

EXAMPLE 8

Large Scale Preparation of Butanoic acid, 3-[[(2E)-2-[(1R,4Z,8S)-8-[[2-O-[4-(acetylethylamino)-2,4-dideoxy-3-O-methyl-a-L-threo-pentopyranosyl]-4,6-dideoxy-4-[[[2,6-dideoxy-4-S-[4-[(6-deoxy-3-O-methyl-a-L-mannopyranosyl)oxy]-3-iodo-5,6-di methoxy-2-methylbenzoyl]-4-thio-β-D-ribo-hexopyranosyl]oxy]amino]-β-D-glucopyranosyl]oxy]-1-hydroxy-10-[(methoxycarbonyl)amino]-11-oxobicyclo[7.3.1]trideca-4,9-diene-2,6-diyn-13-ylidene]ethyl]dithio]-3-methyl-, 2-[(1E)-1-[4-[4-[(2,5-dioxo-1-pyrrolidinyl)oxy]-4-oxobutoxy]phenyl]ethylidene] hydrazide, Followed by Purification To a solution of N-acetyl-calicheamicin (60.2 g, 42.7 mmol) in acetonitrile (900 mL) at 4° C. was added linker intermediate butanoic acid, 3-mercapto-3-methyl-,2-[(E)-1-

[4-[4-[(2, 5-dioxo-1-pyrrolidinyl)oxy]-4-oxobutoxy]-phenyl]ethylidene]hydrazide (38.4 g, 85.4 mmol) in one portion followed by 1-(3-dimethylaminopropyl)-3-ethylcarbodiimide (8.2 g, 42.7 mmol). The bottles containing linker and 1-(3-dimethylaminopropyl)-3-ethylcarbodiimide were rinsed with acetonitrile (300 mL) and added to reaction mixture. Triethylamine (6.5 g, 8.9 mL, 64.1 mmol) was then added to reaction mixture. The reaction mixture (a slurry) was stirred for 1 hour at 4° C. at which point it becomes a yellow solution. The reaction mixture was further diluted with acetonitrile (600 mL) and 20 mM sodium acetate buffer, pH 5.0 (1200 mL) and purified by a reversed phase HPLC column using a gradient of mobile phases A and B. (Mobile phase A: 55:45 (v/v) 20 mM NaOAc buffer pH 5.0 (pH 4.5-5.5): acetonitrile: Mobile phase B: acetonitrile.) The fractions of desired purity were pooled and then subjected to solid phase extraction (SPE). In SPE the purified fractions were loaded onto the column and then washed with a water/acetonitrile mixture and then eluted with acetonitrile to yield concentrated fractions containing product. The resulting fractions were concentrated in vacuo, taken up in ethyl acetate and precipitated by adding hexane. The solids were filtered and dried to provide the title compound as a white solid of 96.9% purity by HPLC. (45.2 g, 60% yield).

Mass Spec:
(M+Na)=1801.4578
$^1$H NMR:
$^1$H NMR (CDCl$_3$+5% CD$_3$OD, 400 MHz): 8.69 (s, 1H, 18C—NH—N=), 7.75 (d, J=8.7 Hz, 2H, 22), 6.95 (d, J=8.7 Hz, 2H, 23), 6.38 (br t, J=7 Hz, 1H, 14), 6.23 (d, J=1.5 Hz, 1H, 8), 5.90 (d, J=9.5 Hz, 1H, 4), 5.80 (dd, J=9.5, 1.5 Hz, 1H, 5), 5.72 (d, J=1.5 Hz, 1H, 1D), 5.63 (br d, J=2.2 Hz, 1H, 1E), 5.03 (dd, J=11.5, 1.6 Hz, 1H, 1B), 4.70 (m, 1H, 5E), 4.61 (d, J=7.8 Hz, 1H, 1A), 4.6 (m, 1H, 3E), 4.49 (m, 1H, 2D), 4.31 (m, 1H, 3B), 4.20 (m, 1H, 5D), 4.10 (m, 2H, 25), 4.07 (m, 1H, 5B), 4.03 (m, 1H, 3A), 3.91 (m, 1H, 15), 3.89 (s, 3H, 2C—OCH$_3$), 3.84 (s, 3H, 3C—OCH$_3$), 3.8 (m, 1H, 3D), 3.76 (m, 1H, 15), 3.75 (m, 1H, 4B), 3.65 (m, 1H, 5A), 3.63 (bs, 3H, 10-NHCOOCH$_3$), 3.62 (m, 1H, 2A), 3.6 (m, 1H, 4D), 3.57 (s, 3H, 3D-OCH$_3$), 3.4 (m, 1H, 5E), 3.37 (s, 3H, 3E-OCH$_3$), 3.30 (m, 2H, 4E-N—CH$_2$CH$_3$), 3.12 (d, J=17.6 Hz, 1H, 12), 3.0 (m, 1H, 4E), 2.85 (m, 2H, 27), 2.85 (bs, 4, 30), 2.72 (d, J=17.6 Hz, 1H, 12), 2.5 (m, 2H, 17), 2.4 (m, 1H, 2E equatorial), 2.33 (m, 1H, 4A), 2.25 (m, 2H, 26), 2.18 (s, 3H, 19), 2.08 (s, 3H, 4E-N—COCH$_3$), 2.0 (m, 1H, 2B), 1.8 (m, 1H, 2B), 1.50 (s, 3H, 16a), 1.44 (s, 3H, 16b), 1.42 (d, J=6.2 Hz, 3H, 6B), 1.4 (m, 1H, 2E axial), 1.31 (d, J=6.1 Hz, 3H, 6A), 1.31 (d, J=6.1 Hz, 3H, 6D), 1.19 (t, J=7.2 Hz, 3H, 4E-N—CH$_2$CH$_3$)

What is claimed is:
1. A compound of Formula I

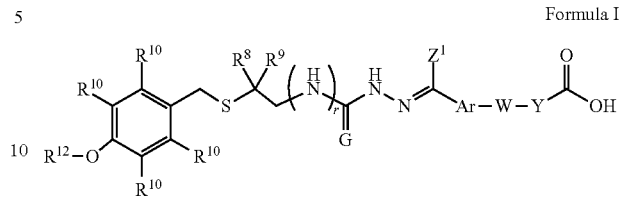

Formula I wherein $R^{12}$ is selected from straight and branched-chain $C_1$-$C_8$ alkyl;
each $R^{10}$ is independently selected from hydrogen, $R^{12}$ and —$OR^{12}$;
$R^8$ and $R^9$ are each independently selected from hydrogen and straight and branched-chain $C_1$-$C_8$ alkyl, wherein each said alkyl for $R^8$ and $R^9$ is independently optionally substituted by —NH$_2$, —NHR$^{11}$, —NR$^{11}$R$^{13}$, —OR$^{11}$, —OH, or —SR$^{11}$, wherein each $R^{11}$ and each $R^{13}$ are independently selected from straight and branched-chain $C_1$-$C_5$ alkyl;
r is an integer 0 or 1;
G is oxygen or sulfur;
$Z^1$ is H or straight or branched-chain $C_1$-$C_5$ alkyl;
Ar is 1,2-, 1,3-, or 1,4-phenylene optionally substituted with one, two or three groups independently selected from straight or branched-chain $C_1$-$C_6$ alkyl, —OR$^{14}$, —SR$^{14}$, halogen, nitro, —COOR$^{14}$, —C(=O)NHR$^{14}$, —O(CH$_2$)$_n$COOR$^{14}$, —S(CH$_2$)$_n$COOR$^{14}$, —O(CH$_2$)$_n$C(=O)NHR$^{14}$, and —S(CH$_2$)$_n$C(=O)NHR$^{14}$, or Ar is a 1,2-, 1,3-, 1,4-, 1,5-, 1,6-, 1,7-, 1,8-, 2,3-, 2,6-, or 2,7-naphthylidene optionally substituted with one, two, three, or four groups independently selected from straight or branched-chain $C_1$-$C_6$ alkyl, —OR$^{14}$, —SR$^{14}$, halogen, nitro, —COOR$^{14}$, —C(=O)NHR$^{14}$, —O(CH$_2$)$_n$COOR$^{14}$, —S(CH$_2$)$_n$COOR$^{14}$, —O(CH$_2$)$_n$C(=O)NHR$^{14}$, and —S(CH$_2$)$_n$C(=O)NHR$^{14}$;
wherein each $R^{14}$ is independently selected from ($C_1$-$C_5$) alkyl and each $R^{14}$ is independently optionally substituted with one or two groups selected from —OH, —($C_1$-$C_4$)alkyl, and —S($C_1$-$C_4$)alkyl;
each n is an integer independently selected from 0, 1, 2, 3, 4, and 5;
W is selected from —O—, —S—, —C(=O)NH—, —NHC(=O)—, and —NR$^{15}$—, wherein $R^{15}$ is a ($C_1$-$C_5$)alkyl and $R^{15}$ is optionally substituted with one or two groups selected from —OH, —($C_1$-$C_4$)alkyl, and —S($C_1$-$C_4$)alkyl; and
Y is a straight or branched-chain ($C_1$-$C_6$)alkylene group or a straight or branched-chain ($C_2$-$C_6$)alkenylene group.
2. A compound of claim 1, wherein each $R^{10}$ is hydrogen.
3. A compound of claim 2, wherein $R^{12}$ is methyl.
4. A compound of claim 3 having the structure

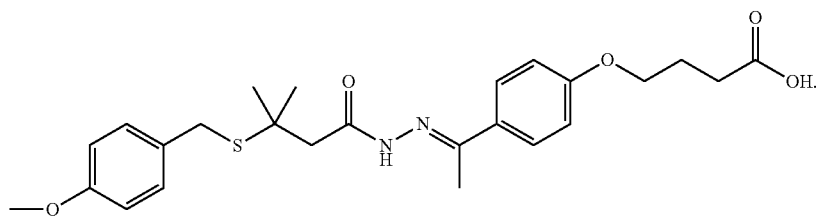 [SMILES: COc1ccc(CSC(C)(C)CC(=O)N/N=C(\C)c2ccc(OCCCC(=O)O)cc2)cc1]

5. A compound of claim 1, wherein $R^8$ and $R^9$ are methyl, r is 0, G is oxygen, $Z^1$ is methyl, Ar is 1,4-phenylene, W is —O—, and Y is —(CH$_2$)$_3$—.

\* \* \* \* \*